(12) United States Patent
Kim et al.

(10) Patent No.: US 11,504,186 B2
(45) Date of Patent: Nov. 22, 2022

(54) METHOD FOR DETERMINING LENS AND APPARATUS USING THE METHOD

(71) Applicant: VISUWORKS, Seoul (KR)

(72) Inventors: Jin Kuk Kim, Seoul (KR); Ik Hee Ryu, Seoul (KR)

(73) Assignee: VISUWORKS, Seoul (KR)

( * ) Notice: Subject to any disclaimer, the term of this patent is extended or adjusted under 35 U.S.C. 154(b) by 0 days.

(21) Appl. No.: 17/067,671

(22) Filed: Oct. 10, 2020

(65) Prior Publication Data
US 2021/0059756 A1    Mar. 4, 2021

Related U.S. Application Data

(63) Continuation of application No. PCT/KR2019/010960, filed on Aug. 27, 2019.

(51) Int. Cl.
| | |
|---|---|
| *A61B 34/10* | (2016.01) |
| *A61F 2/16* | (2006.01) |
| *A61B 3/10* | (2006.01) |
| *A61B 3/117* | (2006.01) |
| *G16H 50/20* | (2018.01) |
| *G16H 50/70* | (2018.01) |
| *G16H 40/20* | (2018.01) |
| *G16H 10/60* | (2018.01) |
| *G16H 50/30* | (2018.01) |
| *G16H 20/40* | (2018.01) |

(52) U.S. Cl.
CPC ............ *A61B 34/10* (2016.02); *A61B 3/1005* (2013.01); *A61B 3/117* (2013.01); *A61F 2/16* (2013.01); *G16H 10/60* (2018.01); *G16H 20/40* (2018.01); *G16H 40/20* (2018.01); *G16H 50/20* (2018.01); *G16H 50/30* (2018.01); *G16H 50/70* (2018.01); *A61B 2034/102* (2016.02); *A61B 2034/108* (2016.02)

(58) Field of Classification Search
None
See application file for complete search history.

(56) References Cited

U.S. PATENT DOCUMENTS

| | | |
|---|---|---|
| 5,724,258 A | 3/1998 | Roffman |
| 2006/0274262 A1 | 12/2006 | Andino et al. |
| 2014/0025165 A1 | 1/2014 | Suzuki et al. |
| 2018/0296320 A1* | 10/2018 | Gupta .................. A61B 3/0025 |
| 2019/0164647 A1 | 5/2019 | Rosen |
| 2021/0000542 A1* | 1/2021 | Bor ...................... A61B 3/0025 |

FOREIGN PATENT DOCUMENTS

| | | |
|---|---|---|
| EP | 3491996 A1 | 6/2019 |
| JP | 2018051223 A | 4/2018 |
| KR | 10-1971747 B1 | 4/2019 |
| WO | 2011026068 A2 | 3/2011 |

OTHER PUBLICATIONS

Sramka et al. (Peer J (2019) vol. 7:23 pages).*
Lee et al. (American Academy of Ophthalmology (2017) Editorial; pp. 1726-1728).*
Nakamura et al. in American Journal of Ophthalmology (2018) vol. 187:99-107).*
Guell et al. (Journal of Refractive Surgery (2010) vol. 36:1976-1993).*
International Search Report in PCT Application No. PCT/KR2019/010960 dated May 26, 2020.
Written Opinion in PCT Application No. PCT/KR2019/010960 dated May 26, 2020.

* cited by examiner

*Primary Examiner* — Lori A. Clow
(74) *Attorney, Agent, or Firm* — Maschoff Brennan

(57) ABSTRACT

A method for determining a lens and apparatus using the method are disclosed. According to an embodiment, a method for determining a lens to be inserted into an eyeball during lens implant surgery using machine learning may be provided, the method comprising: obtaining a plurality of examination data of a person to be operated on; and determining a size of a lens to be inserted into an eyeball of the person among a plurality of lens sizes by inputting the obtained plurality of examination data of the person to a lens determination model, wherein the lens determination model is different from a formula for determining a lens to be inserted into an eyeball during lens implant surgery, and is trained based on examination data of patients who have had lens implant surgery in the past and size information of lenses inserted into eyeballs of the patients.

6 Claims, 27 Drawing Sheets

METHOD FOR DETERMINING LENS AND APPARATUS USING THE METHOD

TECHNICAL FIELD

The following embodiments relate to a method of determining a lens used for lens implant surgery and a device using the same, and more particularly, to a method and device for determining a lens used for lens implant surgery using artificial intelligence.

BACKGROUND ART

Intraocular lens implant surgery, which is one of surgery methods that correct degraded uncorrected vision due to ametropia, is for inserting a special lens, which is designed to correct a refractive disorder, into a normal eyeball with a crystalline lens.

In the related art, during lens implant surgery, a lens is selected using a program provided by a lens manufacturer. In this case, only basic eyeball-related values of a person to be operated on are used as input data, and the size and power of the lens are determined without considering characteristics of an eyeball of the person to be operated on. In general, a program provided by a lens manufacturer is made based on a simple formula, and in the formula, only basic eyeball-related values of a person to be operated on are used as input data. As a result, since many side effects such as cataract and glaucoma are caused due to the insertion of a lens with an inappropriate size and power, the person to be operated on should undergo revision surgery such as surgery for removing a lens.

Recently, various research on lens implant surgery has been conducted to prevent side effects and improve the quality of vision.

DISCLOSURE

Technical Problem

One object relates to provide information about an implantable lens suitable for characteristics of an eyeball of a person to be operated on with lens implant surgery by using machine learning.

One object relates to provide a lens determination assistance system using artificial intelligence and a lens determination assistance process using artificial intelligence.

One object relates to determine a lens more suitable for a person to be operated on with lens implant surgery in consideration of characteristics of an eyeball of each person to be operated on, reduce the probability of occurrence of side effects of the lens implant surgery, and improve quality of vision.

Objects may not be limited to the above, and other objects will be clearly understandable to those having ordinary skill in the art from the disclosures provided below together with accompanying drawings.

Technical Solution

According to an embodiment, it is possible to provide a method of determining a lens to be inserted into an eyeball of a person to be operated on during lens implant surgery through a lens determination model trained using machining learning.

Technical solutions may not be limited to the above, and other technical solutions will be clearly understandable to those having ordinary skill in the art from the disclosures provided below together with accompanying drawings.

Advantageous Effects

According to an embodiment, by determining a lens having a lens size and a lens power suitable for an eyeball of a person to be operated on with lens implant surgery, it is possible to minimize occurrence of side effects after surgery.

According to an embodiment, by determining a lens having a lens size and a lens power suitable for an eyeball of a person to be operated on with lens implant surgery, it is possible to prevent revision surgery from needing to be performed for lens implant surgery.

Advantageous effects may not be limited to the above, and other effects will be clearly understandable to those having ordinary skill in the art from the disclosures provided below together with accompanying drawings.

DESCRIPTION OF DRAWINGS

FIG. 25 shows an example that occurs in a conical incision process of a person to be operated on.

BEST MODE

Figure 1:
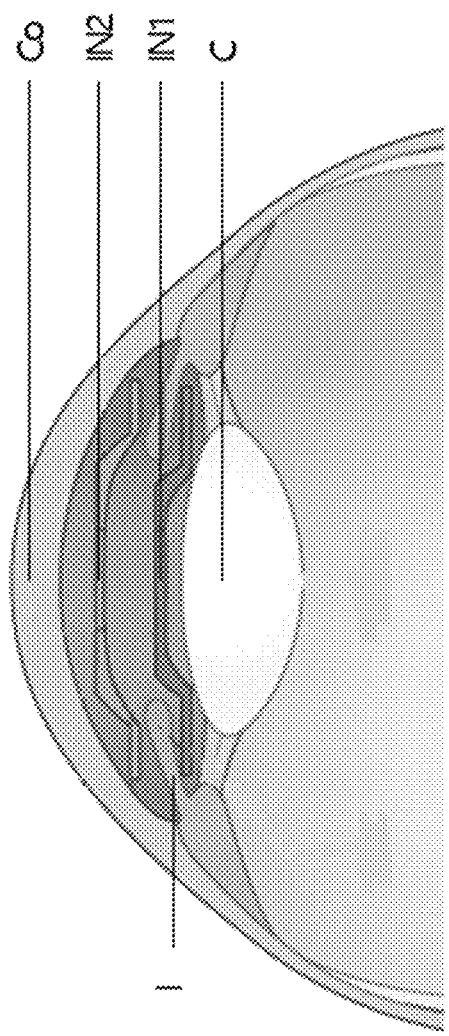
FIG. 1 is a diagram for describing a position at which a lens is inserted during lens implant surgery.

According to an embodiment, a method for determining a lens to be inserted into an eyeball during lens implant surgery using machine learning may comprise obtaining a plurality of examination data of a person to be operated on; and determining a size of a lens to be inserted into an eyeball of the person among a plurality of lens sizes by inputting the obtained plurality of examination data of the person to a lens determination model, wherein the lens determination model may be different from a formula for determining a lens to be inserted into an eyeball during lens implant surgery, and may be trained based on examination data of patients who have had lens implant surgery in the past and size information of lenses inserted into eyeballs of the patients.

Mode for Invention

According to an embodiment, a method for determining a lens to be inserted into an eyeball during lens implant surgery using machine learning may comprise obtaining a plurality of examination data of a person to be operated on; and determining a size of a lens to be inserted into an eyeball of the person among a plurality of lens sizes by inputting the obtained plurality of examination data of the person to a lens determination model, wherein the lens determination model may be different from a formula for determining a lens to be inserted into an eyeball during lens implant surgery, and may be trained based on examination data of patients who have had lens implant surgery in the past and size information of lenses inserted into eyeballs of the patients.

The plurality of examination data of the person may include one of a first data and a second data, and a priority of the first data may be higher than the priority of the second data, wherein the priority may be a priority of an input data to increase an accuracy of a lens size determined by inputting the input data to the lens determination model.

The determining the size of the lens may include when the plurality of examination data of the person does not include the first data and include the second data, determining the size of the lens to be inserted into the eyeball of the person by inputting the second data to the lens determination model, and an accuracy of a lens size determined when the plurality of examination data of the person includes the first data may be higher than an accuracy of a lens size determined when the plurality of examination data of the person includes the second data instead of the first data.

The determining the size of the lens may include calculating a reliability of an accuracy of a lens size derived according to the plurality of examination data of the person, and determining the size of the lens by providing the calculated reliability to a user.

According to an embodiment, the method may further comprise when the plurality of examination data of the person includes the second data or other data except the first data, estimating the first data from the second data or the other data, and in the estimating, an accuracy corresponding to a lens size derived when the first data is inputted to the lens determination model may be higher than an accuracy corresponding to a lens size derived when the second data is inputted to the lens determination model.

The first data among the plurality of examination data of the person may include ATA (Anterior Chamber Angle), ACD-epi (Anterior Chamber Depth), ACD-endo, CCT (Central Conical Thickness), CLR (crystalline lens rise), WTW, Axial Length, BUT, a distance between iris, and a space size value for a lens, and the first data is obtained by using a laser and/or a high-frequency ultrasound, and the second data may be obtained by using a general ophthalmic examination.

In the determining the size of the lens, a size of a lens to be inserted into an eyeball of the person may be determined as any one of a plurality of predetermined lens sizes.

In the determining the size of the lens, a size of a lens may be determined as any one of non-standardized lens sizes derived by inputting the plurality of examination data to the lens determination model, not a plurality of predetermined lens sizes.

According to an embodiment, the method may further comprise determining a lens power to be inserted into an eyeball of the person among a plurality of lens powers by inputting the obtained plurality of examination data of the person to the lens determination model, wherein in the determining the lens power, the lens power may be determined so that a target vision of the person is derived when a lens determined by the lens determination model is inserted into the eyeball of the person, and wherein the lens determination model may be trained based on examination data of patients who have had lens implant surgery in the past and incision information of the patients.

The obtained plurality of examination data of the person may include a diopter, an astigmatism axis and an astigmatism direction parameter measured from the eyeball of the person, and the determining the lens power may include determining the lens power suitable for the target vision of the person by inputting the plurality of examination data of the person and incision information expected during a corneal incision process of the person's lens implant surgery to the lens determination model.

When the plurality of examination data of the person is inputted to the lens determination model, a lens power to derive the target vision of the person and incision information expected during a conical incision process of the person's lens implant surgery may be determined.

The incision information may include at least one selected from the group of a conical incision method, a conical incision location, a conical incision direction and/or a corneal incision degree, a location of coma, a corneal astigmatism, a lenticular astigmatism, a ratio of myopia and astigmatism during a corneal incision process of the lens implant surgery.

According to an embodiment, a device for determining a lens to be inserted into an eyeball during lens implant surgery using machine learning, the device may comprising: a memory for storing a plurality of examination data of a person to be operated on; and a processor, wherein the processor may be configured to obtain the stored plurality of examination data of the person from the memory, and determine a size of a lens to be inserted into an eyeball of the person among a plurality of lens sizes by inputting the obtained plurality of examination data of the person to a lens determination model, and wherein the lens determination model may be different from a formula for determining a lens to be inserted into an eyeball during lens implant surgery, and may be trained based on examination data of patients who have had lens implant surgery in the past and size information of lenses inserted into eyeballs of the patients.

According to an embodiment, a method for predicting a vaulting value representing a distance between a rear surface of a lens to be inserted into an eyeball of a person to be operated on with lens implant surgery and an anterior surface of a crystalline lens may comprise: inputting a plurality of examination data of the person to be operated on and one or more lens sizes to a vaulting value prediction model; and predicting the vaulting value corresponding to each of the one or more input lens sizes from the vaulting value prediction model, wherein the vaulting value prediction model may be trained based on a plurality of examination data of patients who have had lens implant surgery in the past, size information of lenses inserted into eyeballs of the patients, and vaulting values measured after surgery of the patients.

The vaulting value may be defined as the shortest distance among a plurality of distances between the rear surface of the lens to be inserted into the eyeball of the person to be operated on with the lens implant surgery and the anterior surface of the crystalline lens.

The predicting of the vaulting value may include providing information about whether the input lens size is suitable for the lens to be inserted into the eyeball of the person to be operated on according to whether the predicted vaulting value satisfies a condition of a predetermined range.

When the predicted vaulting value satisfies the condition of the predetermined range, information may be provided that the input lens size is suitable for the lens to be inserted into the eyeball of the person to be operated on, and when the predicted vaulting value does not satisfy the condition of the predetermined range, information may be provided that the input lens size is not suitable for the lens to be inserted into the eyeball of the person to be operated on.

The condition of the predetermined range may satisfy the predicted vaulting value being included within a range of 250 to 750 μm.

According to an embodiment, a method for predicting a vaulting value representing a distance between a rear surface of a lens to be inserted into an eyeball of a person to be operated on with lens implant surgery and an anterior surface of a crystalline lens may comprise: inputting a plurality of examination data of the person to be operated on to a vaulting value prediction model; and predicting expected lens sizes suitable for the eyeball of the person to be operated on and the vaulting value corresponding to each of the expected lens sizes from the vaulting value prediction model, wherein the vaulting value prediction model may be trained based on a plurality of examination data of patients who have had lens implant surgery in the past, sizes of lenses inserted into eyeballs of the patients, and vaulting values measured after surgery of the patients.

The expected lens size suitable for the eyeball of the person to be operated on may include any one selected from a plurality of preset lens sizes.

The expected lens size suitable for the eyeball of the person to be operated on may include any one selected from non-standardized lens sizes rather than the plurality of preset lens sizes.

According to an embodiment, a device for predicting a vaulting value representing a distance between a rear surface of a lens to be inserted into an eyeball of a person to be operated on with lens implant surgery and an anterior surface of a crystalline lens may comprise: a memory, which stores a plurality of examination data of the person to be operated on; and a processor, wherein the processor may input the plurality of examination data of the person to be operated on and one or more lens sizes to a vaulting value prediction model and may predict the vaulting value corresponding to each of the one or more input lens sizes from the vaulting value prediction model, and the vaulting value prediction model may be trained based on a plurality of examination data of patients who have had lens implant surgery in the past, sizes of lenses inserted into eyeballs of the patients, and vaulting values measured after surgery of the patients.

Hereinafter, specific embodiments of the present invention will be described in detail with reference to the accompanying drawings. Meanwhile, the spirit of the present invention is not limited to the suggested embodiments, and those skilled in the art to which the present invention pertains could easily suggest a more retrogressive invention or another embodiment which falls within the spirit of the present invention through the addition, modification, and deletion of another component without departing from the spirit of the present invention.

The same reference numerals will be used throughout to designate the same or like components having the same function within the same scope shown in the drawings of the embodiments.

1. DEFINITION OF TERMS (1) Lens Implant Surgery

Lens implant surgery is one of surgery methods that correct degraded uncorrected vision due to ametropia and is a surgery for inserting a special lens, which is designed to correct a refractive disorder, into a normal eyeball with a crystalline lens.

FIG. 1 is a diagram for describing a position at which a lens is inserted during lens implant surgery. As types of lens implant surgery, there are anterior chamber lens implant surgery in which a lens is inserted between a cornea Co and an iris I and posterior chamber lens implant surgery in which a lens is inserted into a space between a back of an iris and a crystalline lens. Referring to FIG. 1, in the posterior chamber lens implant surgery, a lens may be inserted at a position IN1 (first lens insertion portion), and in the anterior chamber lens implant surgery, a lens may be inserted at a position IN2 (second lens insertion portion). Hereinafter, for convenience of description, the present invention will be described based on the posterior chamber lens implant surgery that is also referred to as implantable collamer lens (ICL) implant surgery. However, the present invention is not limited thereto, and of course, the present invention may be applied to the anterior camber lens implant surgery.

(2) Lens

In the present specification, a lens may refer to an intraocular lens used in lens implant surgery and may be distinguished from a hard lens and a soft lens worn on an eyeball surface.

Information about the lens may include information about a lens size and information about a lens power. The lens size may include a plurality of lens sizes. The lens power may include a plurality of lens powers. In addition, the expression "lens determination" may refer to the determination of any one of combinations of a plurality of lens sizes and a plurality of lens powers.

(3) Lens Determination Model

A lens determination model refers to an algorithm and/or model that determine an intraocular lens inserted into an eyeball using artificial intelligence. When examination data of a person to be operated on is input as input data through the model, a lens determination model described below is a model for deriving information about a lens to be inserted into an eyeball of the person to be operated on as output data corresponding to the input data. Hereinafter, a configuration, generation process, and determination process of a lens determination model will be described in detail.

(4) Learning

Learning refers to a process in which a lens determination model is trained based on learning data and labeling data or unlabeled data to determine output data with respect to input data. That is, the lens determination model forms a rule to determine the data.

The lens determination model may be trained through learning data. Training the lens determination model means adjusting a weight of the model.

As learning methods, there are various methods including supervised learning, unsupervised learning, reinforcement learning, and imitation learning.

2. LENS DETERMINATION ASSISTANCE SYSTEM

2.1. Configuration of Lens Determination Assistance System

Figure 2:
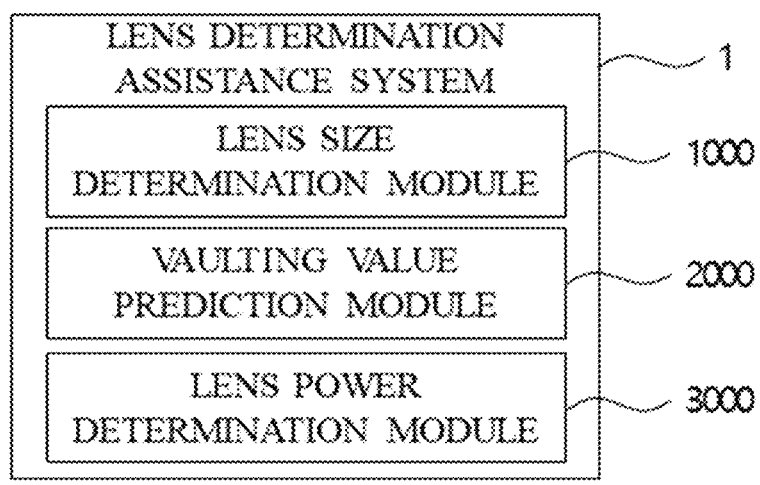
FIG. 2 is a diagram illustrating a lens determination assistance system according to an embodiment.

FIG. 2 illustrates a lens determination assistance system 1 according to an embodiment. Referring to FIG. 2, the lens determination assistance system 1 may include a lens size determination module 1000 which derives a lens size of information about a lens to be inserted into an eyeball of a person to be operated on, a vaulting value prediction module 2000 which assists in determining the lens size, and a lens power determination module 3000 which derives a lens power.

The lens determination assistance system 1 may perform functions of determining a lens size, predicting a vaulting value, and determining a lens power. Specifically, the lens determination assistance system 1 may determine a lens size, predict a vaulting value, and determine a lens power using a lens determination model trained through machine learning.

Of course, in FIG. 2, the lens determination assistance system 1 is illustrated as including all of the lens size determination module 1000, the vaulting value prediction module 2000, and the lens power determination module 3000, but not limited thereto. In some cases, the lens determination assistance system may include at least one selected from the group of the lens size determination module, the vaulting value prediction module, and the lens power determination module.

In addition, the lens size determination module 1000, the vaulting value prediction module 2000, and the lens power determination module 3000 may be implemented in one device or different devices. For example, when the lens size determination module configured to derive a lens size in the lens determination assistance system 1 is implemented in any one device, only size information of the lens to be inserted into the eyeball of the person to be operated on may be acquired.

Alternatively, in the lens determination assistance system 1, at least two modules of the lens size determination module, the vaulting value prediction module, and the lens power determination module may be implemented to inter-work with each other. For example, in order to acquire size information of a lens to be inserted into an eyeball of a person to be operated on, the lens size determination module and the vaulting value prediction module may be combined and may be implemented to interwork with each other, thereby deriving a vaulting value that is predicted together with a size of a lens to be inserted. Hereinafter, each module of the lens determination assistance system will be described one by one.

Figure 3:
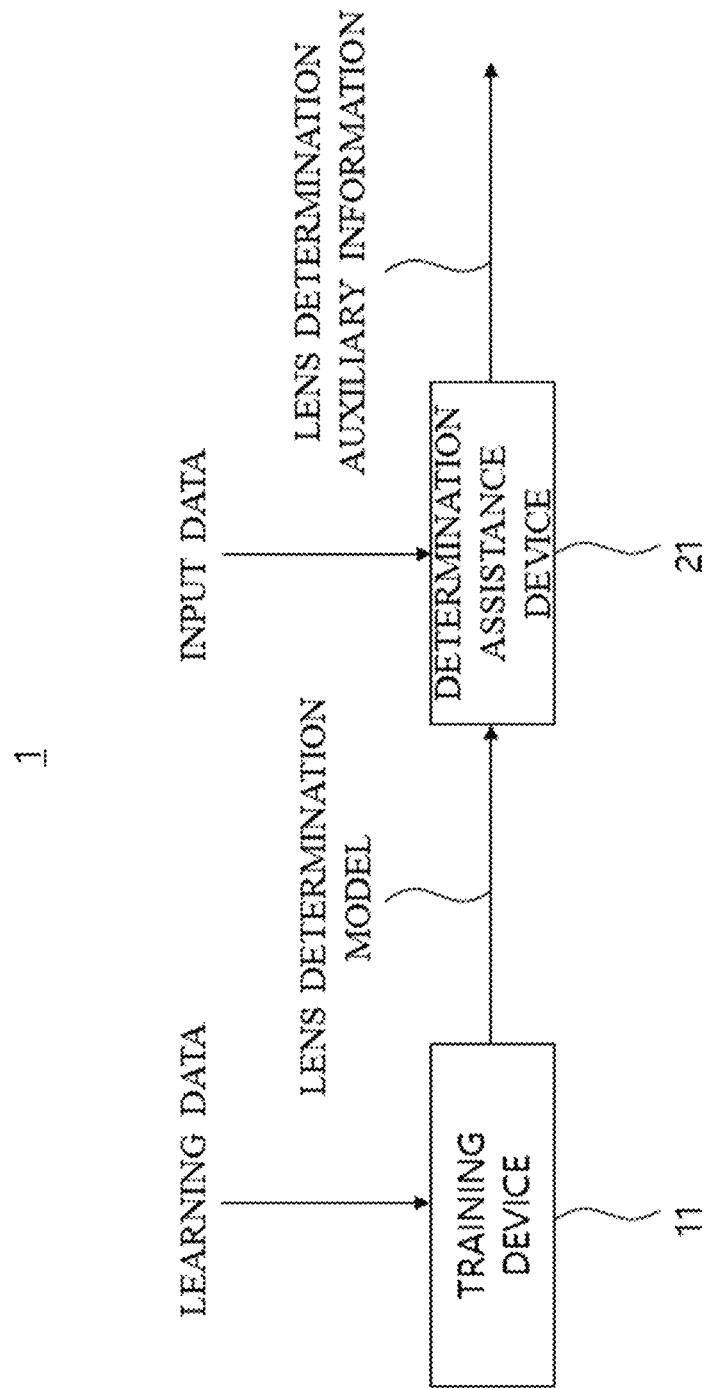
FIG. 3 is a diagram illustrating a lens determination assistance system according to another embodiment.

FIG. 3 is a diagram illustrating a configuration of a training device 11 and a determination assistance device 21 of the lens determination assistance system 1. In an embodiment, the lens determination assistance system 1 may include the training device 11 and the determination assistance device 21.

The training device 11 may train the lens determination model. Specifically, the training device 11 may train the lens determination model based on learning data. The training device 11 may train the lens determination model through various learning methods. For example, the training device 11 may train the lens determination model through methods including supervised learning, unsupervised learning, reinforcement learning, and imitation learning. The training device 11 may train the lens determination model by providing labeled data for the learning data. However, the labeled data is not necessarily used, and unlabeled data may be used.

The determination assistance device 21 may receive the trained lens determination model from the training device 11 to use the trained lens determination model. Specifically, the determination assistance device 21 may output auxiliary information for determining a lens to be inserted into an eyeball of a person to be operated on using the trained lens determination model. Specifically, when receiving input data such as examination data of the person to be operated on, the determination assistance device 21 may output information about a lens suitable for an eyeball of the person to be operated on. The determination assistance device 21 may enable a user to determine a lens to be inserted into the eyeball of the person to be operated on with lens implant surgery through the output information about the lens.

The information about the lens may be information about a lens size, a predicted vaulting value, and a lens power.

The lens determination model trained using the learning data in the training device 11 may be transmitted to the determination assistance device 21. Of course, in FIG. 3, the training device 11 and the determination assistance device 21 are illustrated as being separated, but not limited thereto. In some cases, the training device 11 and the determination assistance device 21 may be implemented to be separated and may be implemented as one without being separated. As an example, the determination assistance device may be the same device as the training device or may be a device separate from the training device.

Figure 4:
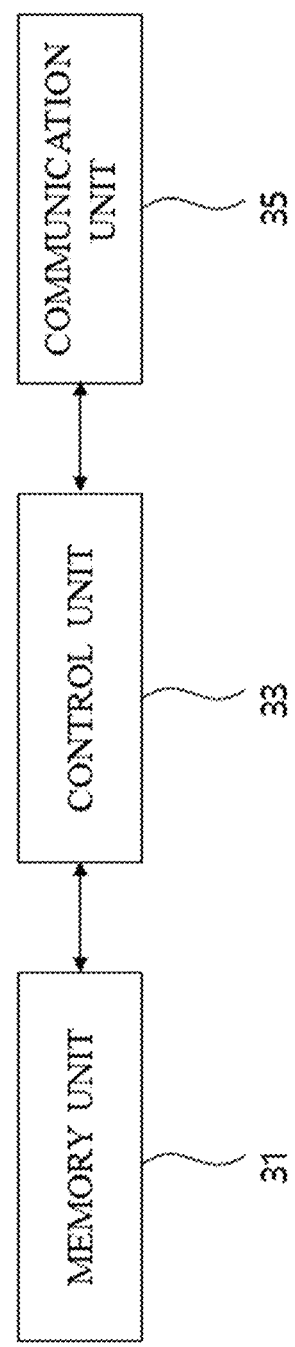
FIG. 4 is a diagram illustrating a lens determination assistance system according to another embodiment.

FIG. 4 is a diagram illustrating a configuration of the training device and/or the determination assistance device. Referring to FIG. 4, the training device and/or the determination assistance device may include a memory unit 31, a control unit 33, and a communication unit 35.

The training device and/or the determination assistance device may include the control unit 33. The control unit 33 may control operations of the training device and/or the determination assistance device. The control unit 33 may read a system program and various processing programs stored in the memory unit 31.

The control unit 33 may include one or more of a central processing unit (CPU), a random access memory (RAM), a graphic processing unit (GPU), one or more microprocessors, and other electronic components capable of processing input data according to preset logic.

The training device and/or the determination assistance device may include the memory unit 31. The memory unit 31 may store data and a learning model which are required for learning. The memory unit 31 may store examination data of a person to be operated on.

The memory unit 31 may store learning data, labeling data, unlabeled data, input data, output data, and the like.

The memory unit 31 may be implemented using a nonvolatile semiconductor memory, a hard disk, a flash memory, a RAM, a read-only memory (ROM), an electrically erasable programmable ROM (EEPROM), or other tangible nonvolatile recording media.

The memory unit 31 may store various processing programs, parameters for processing programs, result data of such processing, or the like.

The training device and/or the determination assistance device may further include the communication unit 35. The communication unit 35 may communicate with an external device. The communication unit 35 may perform wired or wireless communication. The communication unit 35 may perform bidirectional or unidirectional communication.

The training device and/or the determination assistance device may include a processor, a volatile memory, a nonvolatile memory, a mass storage device, and a communication interface. The processor may perform training on the lens determination model through the training device and/or the determination assistance device.

Figure 5:
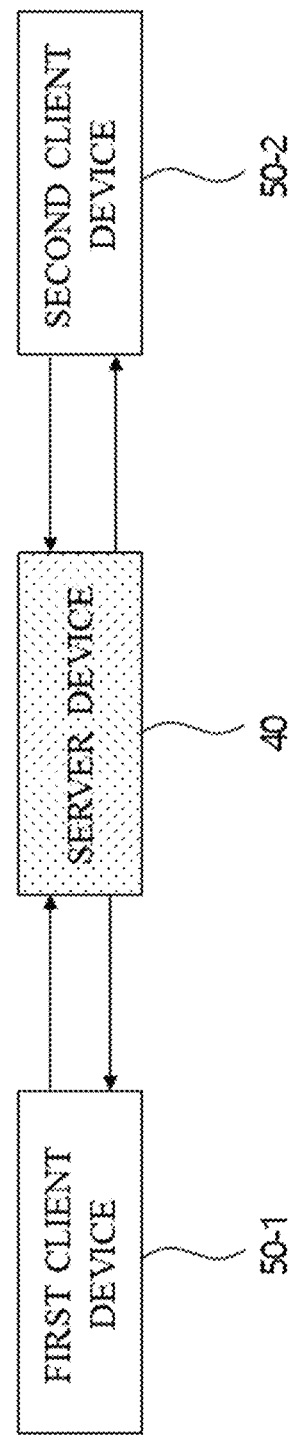
FIG. 5 is a diagram illustrating a lens determination assistance system using a server.

FIG. 5 is a schematic diagram illustrating a lens determination assistance system using a server. Referring to FIG. 5, the lens determination assistance system may include a plurality of client devices and a server device. Hereinafter, a first client device among the plurality of client devices is exemplarily described, but a second client device may perform the same operation.

A first client device 50-1 may request information from a server device 40 and acquire lens determination auxiliary information transmitted in response to the request and may request lens determination auxiliary information from the server device 40.

The first client device 50-1 may acquire data necessary for lens determination and may transmit data acquired from the determination assistance device.

The first client device 50-1 may be a portable device such as a smartphone or a tablet personal computer (PC).

The server device 40 may store and/or drive a lens determination model. The server device 40 may store weights constituting the trained lens determination model. The server device 40 may collect and/or store data used to assist in lens determination.

The server device 40 may output results of a lens determination assistance process using the lens determination model to the first client device 50-1. The server device 40 may acquire feedback from the first client device 50-1.

In an embodiment, the first client device 50-1 may acquire the lens determination model from the server device 40 and drive the acquired lens determination model. In this case, the first client device 50-1 may acquire lens determination auxiliary information by driving the lens determination model without providing input data to the server device 40.

The server device 40 may communicate with the first client device 50-1 configured to acquire first lens determination auxiliary information and/or a second client device 50-2 configured to acquire second lens determination auxiliary information.

Figure 6:
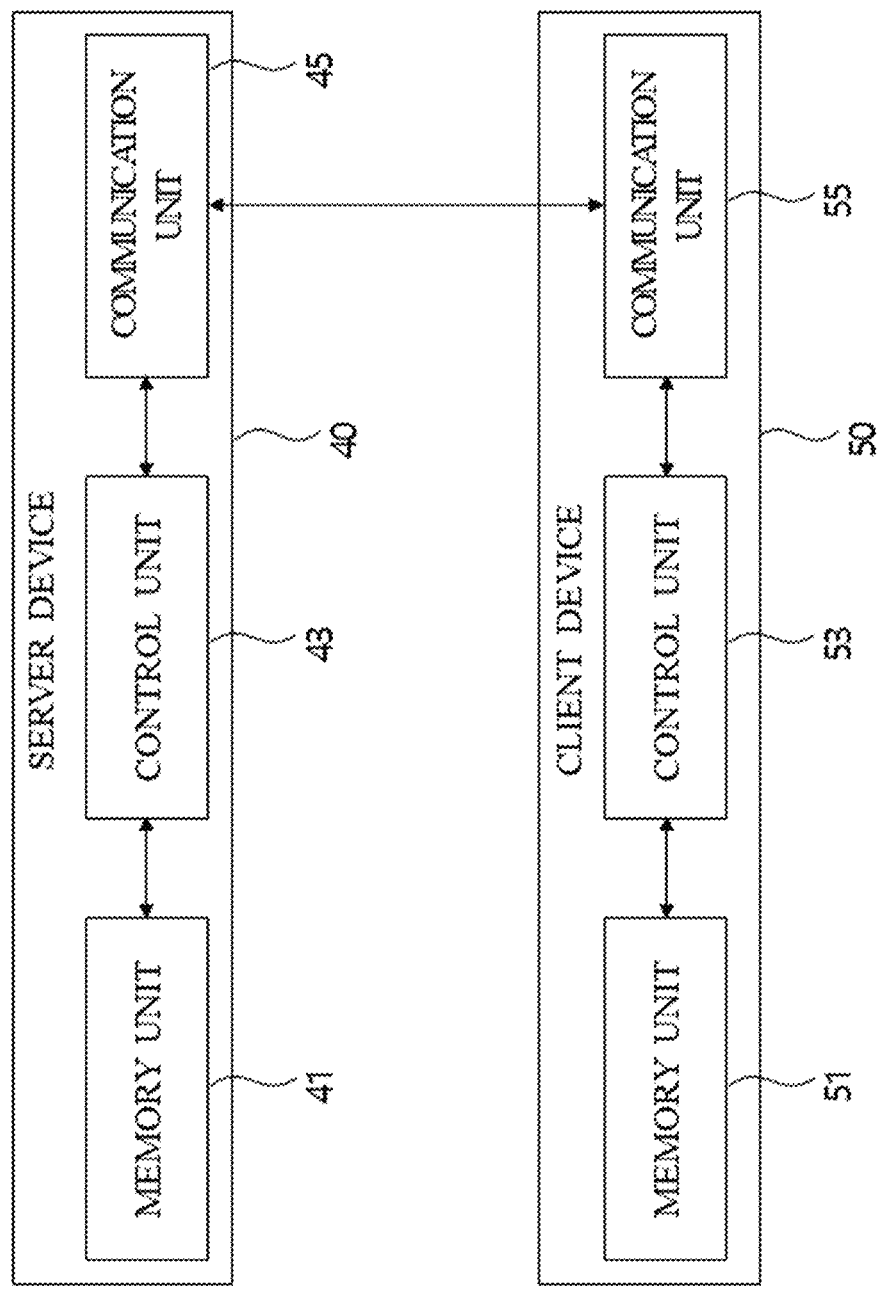
FIG. 6 is a diagram illustrating a relationship between a server device and a client device.

FIG. 6 is a schematic diagram illustrating a relationship between the server device 40 and a client device 50. Referring to FIG. 6, the server device 40 may communicate with the client device 50 through a communication unit. The communication u0nit may perform wired or wireless communication. The communication unit may perform bidirectional or unidirectional communication. The client device 50 may also communicate with the server device 40 through a communication unit.

In an embodiment, when the client device 50 transmits input data of a person to be operated on to the server device, the server device 40 may receive information about a lens to be inserted into an eyeball of the person to be operated on using a trained lens determination model.

In an embodiment, a control unit 53 of the client device 50 may acquire input data from a memory unit 51, and the acquired input data may be transmitted to a communication unit 45 of the server device 40 through a communication unit 55. In addition, a control unit 43 of the server device 40 obtains a result value by inputting input data to a lens determination model stored in a memory unit 41, and the obtained result value may be transmitted to the communication unit 55 of the client device 50 using the communication unit 45.

2.2. Lens Determination Model

Figure 7:
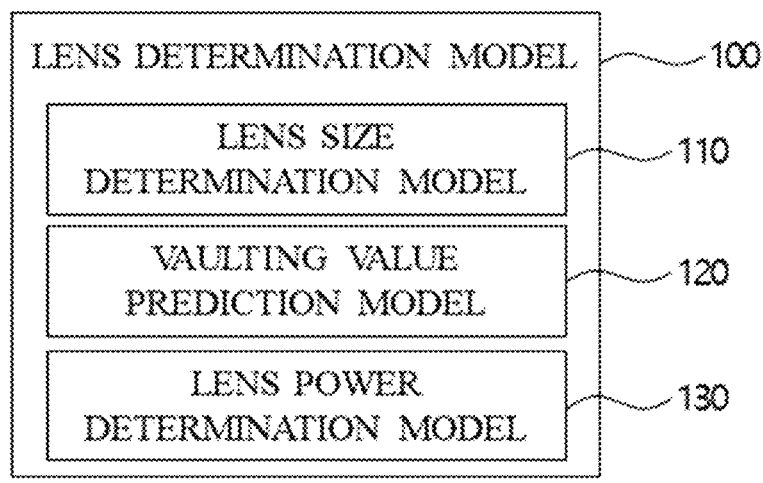
FIG. 7 is a diagram illustrating a lens determination model according to an embodiment.

FIG. 7 is a diagram illustrating a lens determination model. Referring to FIG. 7, a lens determination model 100 may include a lens size determination model 110, a vaulting value prediction model 120, and a lens power determination model 130.

Of course, in FIG. 7, the lens determination model 100 is illustrated as including all of the lens size determination model 110, the vaulting value prediction model 120, and the lens power determination model 130, but not limited thereto. In some cases, the lens determination model 100 may include at least one selected from the group of the lens size determination model, the vaulting value prediction model, and the lens power determination model.

In an embodiment, the lens determination model 100 may include the lens size determination model and the lens power determination model or may include the lens size determination model and the vaulting value prediction model.

In addition, the lens determination model 100 may be implemented in one device or different devices. For example, when the lens determination model includes the lens size determination model and the vaulting value prediction model, the models may be implemented in one device to interwork with each other. Alternatively, when the lens determination model 100 includes the lens size determination model and the lens power determination model, the lens size determination model may be implemented in a different device independently from the lens power determination model.

Figure 8:
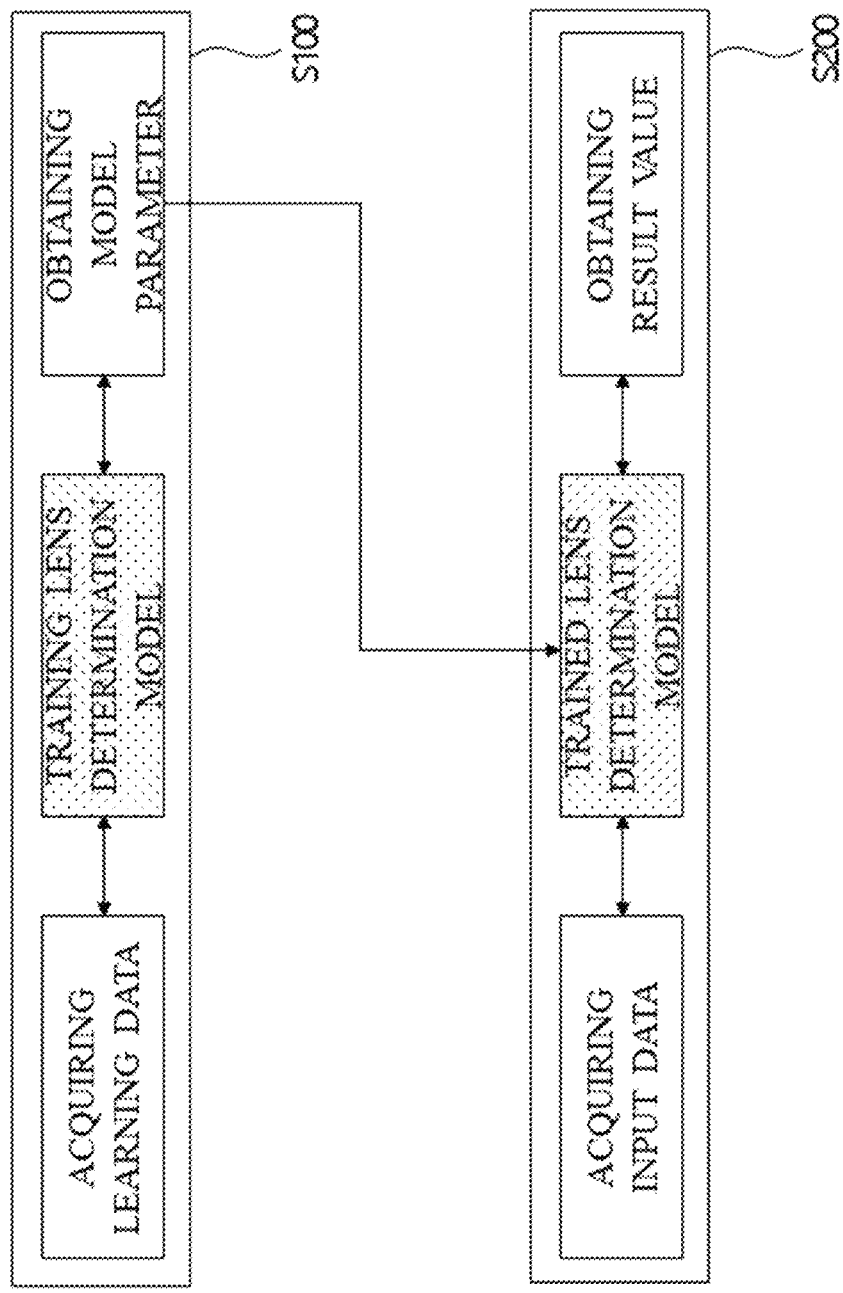
FIG. 8 is a diagram of a lens determination assistance process according to an embodiment.

FIG. 8 is a diagram of a lens determination assistance process. Referring to FIG. 8, the lens determination assistance process may be considered by being mainly divided into a training operation S100 of training a lens determination model and a determining operation S200 of performing a lens determination model using the trained lens determination model.

Referring to FIG. 8, the training operation S100 may be a process of training the lens determination model using learning data. In addition, the training operation S100 may be performed by the training device.

According to an embodiment, in the training operation S100, the learning data may be acquired, and the lens determination model may be trained using the acquired data. That is, the training operation S100 is a process of generating the lens determination model, and model parameters constituting the lens determination model may be obtained according to the generation of the lens determination model. As an example, the model parameters may include weights adjusted when the lens determination model is trained.

In an embodiment, the learning data may include a plurality of examination data of patients who have had lens implant surgery in the past, information about lenses inserted into eyeballs of the patients (lens size and lens power), surgery parameters, and vaulting value data measured after surgery of the patients.

In addition, the examination data of the learning data may include examination data acquired from a plurality of examination apparatuses related to measurement of an eyeball of the patients who have had the lens implant surgery in the past.

In an embodiment, the information about the lens of the learning data may include a lens size and/or a lens power of the lens inserted into the eyeball of the patient who has had the lens implant surgery in the past. In this case, when side effects have not occurred in the patient who has had the lens implant surgery in the past after the lens implant surgery, the information about the lens may include a lens size and/or a lens power of the lens inserted into the eyeball of the patient. Of course, according to some embodiments, when side effects have occurred in the patient who has had the lens implant surgery in the past after the lens implant surgery, the information about the lens may include a lens size and/or a lens power of the lens inserted into the eyeball of the patient.

In addition, the surgical parameters of the learning data may be related to corneal incision information during a corneal incision process of the patient who has had the lens implant surgery in the past. As an example, the surgical parameters may include a corneal incision method, a conical incision location, a corneal incision degree, and the like.

In an embodiment, the vaulting value data of the learning data may refer to a value representing a distance between a rear surface of a lens to be inserted into an eyeball of a person to be operated on with lens implant surgery and an anterior surface of a crystalline lens and may refer to vaulting value data measured on the patient who has had the lens implant surgery in the past.

The lens determination model may be a model that outputs information about a lens based on the learning data. At least one of a plurality of learning algorithms for calculating information about a lens may be selected as the lens determination model. For example, the algorithm may be a logistic regression, a K-nearest neighbor algorithm, a support vector machine, a decision tree, or the like.

The lens determination model may use multiple learning algorithms among a plurality of learning algorithms for calculating a predicted value. For example, an ensemble method may be used in the lens determination model, and better prediction performance may be obtained as compared with when learning algorithms are separately used.

The lens determination model may be implemented in the form of a classifier that generates information about a lens. The classifier may perform double-classification or multi-classification.

The lens determination model may be implemented in the form of a regression so as to derive information of a lens. A regression method may be a linear regression method, a logistic regression method, or the like.

In an embodiment, the training operation S100 may be performed by obtaining a result value (output data) using a model to which arbitrary weights are given, comparing the obtained result value (output data) with labeling data of learning data, and performing backpropagation according to an error to optimize the weights.

Although not shown, the training operation S100 may include an evaluating operation of evaluating performance of the trained lens determination model. In the evaluating operation, the lens determination model may be evaluated using an evaluation data set. The evaluating operation of the lens determination model may be an operation of evaluating the lens determination model trained in the training operation and predicting new data using the lens determination model. Specifically, the evaluation operation may be an operation of measuring whether the trained lens determination model can be generalized to the new data.

In addition, in the training operation S100 of the lens determination model, a learning data set and an evaluation data set may be distinguished. Here, the learning data set may refer to a set of learning data used in a training process of the training operation, and the evaluation data set may refer to a set of evaluation data used in an evaluating process of the evaluating operation. In this case, the learning data set used to train the lens determination model may not be used in the evaluating operation of the lens determination model.

In addition, referring to FIG. 8, the determining operation S200 may use the trained lens determination model trained by obtaining the model parameters in the training operation. Specifically, in the determining operation S200, after input data, such as examination data of the person to be operated on, is acquired, information (result value) about a lens to be inserted into an eyeball of the person to be operated on may be acquired using the trained lens determination model. In addition, the determining operation S200 may be performed by the determination assistance device.

The input data may include a plurality of examination data of the person to be operated on with the lens implant surgery.

The result value may include the information about the lens to be inserted into the eyeball of the person to be operated on. The information about the lens may include a lens size, a lens power, a predicted vaulting value, and the like. Hereinafter, the determination of the lens size, the prediction of the vaulting value, and the determination of the lens power will be described in more detail.

3. DETERMINATION OF LENS SIZE

3.1. Configuration of Lens Size Determination Module

Figure 9:
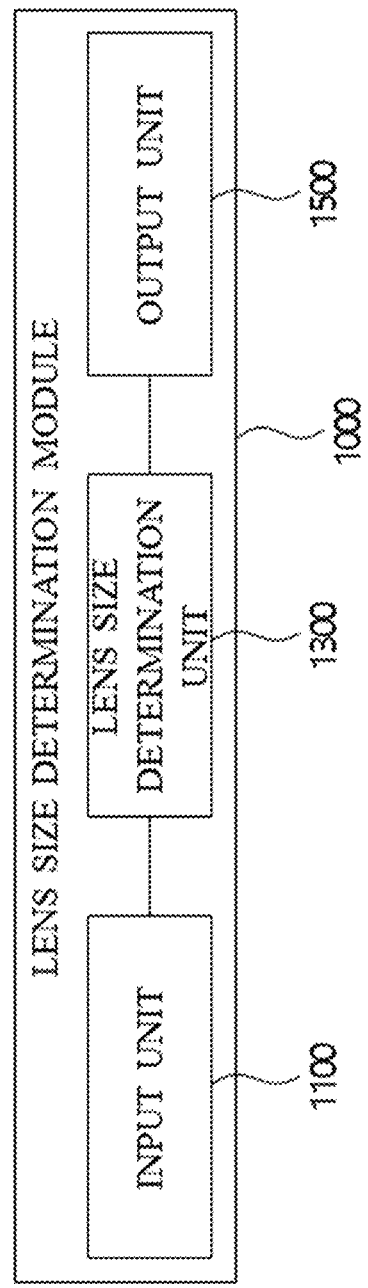
FIG. 9 is a diagram of a lens size determination module according to an embodiment.

FIG. 9 is a diagram illustrating a configuration of the lens size determination module 1000. In an embodiment, the lens size determination module 1000 may output a lens size of a lens to be inserted into an eyeball of a person to be operated on from input data.

Referring to FIG. 9, the lens size determination module 1000 may include an input unit 1100, a lens size determination unit 1300, and an output unit 1500.

The input unit 1100 may acquire input data from a database. Here, the input data may be a plurality of examination data of the person to be operated on.

Specifically, the input unit 1100 may be connected directly to the database to acquire the input data. In addition, the input unit 1100 may receive and acquire the input data from a server or other external devices.

The input data may be the examination data of the person to be operated on. The input data may include a plurality of parameters. Specifically, the input data may include examination data representing different parameters obtained from the same or different examination apparatuses or may include examination data representing the same parameters obtained from different examination apparatuses.

In addition, the input data may include examination data measured at the same time point or may include examination data measured at different time points.

The input data may be the same and/or different parameters obtained from the same examination apparatus or may be the same and/or different parameters obtained from different examination apparatuses.

In addition, the input data may be provided with one piece of input data or a plurality of pieces of input data. The pieces of input data may have different degrees of influence on a result value (lens size of the lens to be inserted into the eyeball of the person to be operated on). In an embodiment, each pieces of input data may include parameters, and a degree to which the input data has an influence on a result value may vary according to types of the parameters included in the pieces of input data. Here, the parameters may be defined to represent characteristics of the eyeball of the person to be operated on and may be expressed numerically. For example, the parameters may include an angle-to-angle (ATA) distance indicating a distance between anterior angles, an anterior chamber depth (ACD)-epi, an ACD-endo, a central corneal thickness (CCT), a crystalline lens rise (CLR), a white-to-white (WTW), an axial length (AL), corneal curvature, a refractive error (myopia, astigmatism, farsightedness degree), a pupil size, an intraocular pressure, vision, a corneal shape, a corneal thickness, an eyeball length, a lens insertion space, and the like.

The person to be operated on may include a person who is to undergo surgery by selecting lens implant surgery among vision correction surgery. The person to be operated on may be a person who is to undergo lens implant surgery using information about a lens output from the lens determination assistance system. A user may be a person who acquires information on a lens to be inserted into an eyeball of the person to be operated on using the lens determination assistance system. For example, the user may include a doctor who performs lens implant surgery, a lens manufacturer, or the like.

The plurality of examination data may be data acquired from a plurality of examination apparatuses which measure an eyeball and may include a plurality of eyeball-related parameters.

In addition, the examination data may include medical inquiry data (interview data). Specifically, the examination data may include target vision and the like desired after the lens implant surgery of the person to be operated on.

Furthermore, the examination data may be measurement data about a cornea. For example, the examination data may include a corneal shape, corneal symmetry, corneal thickness measurement data, corneal structure tomography data, corneal shape analysis data, corneal curvature, corneal endotheliocyte examination data, and the like.

In addition, the examination data may be measurement data about vision and/or refraction. For example, the examination data may include power data of glasses worn in the past, optometry, refractive errors (myopia, astigmatism, and farsightedness degrees), and the like.

In addition, the examination data may be measurement data of a distance in an eyeball. Specifically, the examination data may include a pupil size, an eyeball length, and a distance of a space in which a lens is to be inserted.

In addition, the examination data may be data about eye diseases and/or chronic diseases. For example, the examination data may include data about the presence or absence of retinal diseases, glaucoma, retinal degeneration, or the like, cataract, diseases of a posterior surface of an iris, and the like.

In addition, the examination data may be measurement data about a retina. For example, the examination data may include an image captured by photographing a fundus retina or the like.

The examination data may be measured using one or more apparatuses.

Of course, the plurality of examination data may not be limited to only data acquired from a plurality of apparatuses for measuring an eyeball. In addition to the acquired data, the plurality of examination data may include a variety of data. For example, the examination data may include examination data about eye-related genes, blood, or the like.

When input data, such as the plurality of examination data of the person to be operated on, is inputted, the lens size determination unit 1300 may determine a lens size suitable for the eyeball of the person to be operated on. Here, the suitable lens size may mean a lens size in which the possibility of occurrence of side effects is minimized when lens implant surgery is performed on the person to be operated on. Specific operations of the lens size determination unit 1300 will be described in more detail with reference to FIG. 11.

In an embodiment, the lens size determination unit 1300 may calculate reliability of accuracy of a lens size derived according to the examination data of the person to be operated on. Information about the reliability may be pre-stored or may be provided from the outside. For example, information including that, among the plurality of examination apparatuses, a result value of a first apparatus has a reliability of 90% and a result value of a second apparatus has a reliability of 80% may be received through an external device that stores the information about the reliability in advance. In an embodiment, the lens size determination model 110 may calculate reliability of accuracy of the lens size derived according to the examination data of the person to be operated on based on reliability pre-stored in a training operation. For example, in a case of using examination data measured using the first apparatus, reliability of accuracy of an output lens size may be calculated as 90%, and the calculation result may be presented to a user through the output unit 1500.

The output unit 1500 may output a lens size obtained through the lens size determination unit 1300 to the user. In an embodiment, the output unit 1500 may provide a display that visually outputs output data on a screen. In addition, the output unit 1500 may output various forms such as an image and a text.

The output unit 1500 may output the information (output data) about the lens size of the lens to be inserted into the eyeball of the person to be operated on through the lens size determination unit 1300.

The output unit 1500 may output a standardized lens size according to a learning method of the lens size determination model.

According to an embodiment, when the lens size determination model is implemented in the form of a classifier, the output unit may output a standardized lens size. The standardized lens size may be an existing lens size. The existing lens size may be a size that is predetermined according to a preset standard. For example, the standardized lens size may be 12.1 mm, 12.6 mm, 13.2 mm, 13.7 mm More detailed descriptions thereof will be given in Content 3.3 below. However, it is not limited thereto, and when the lens size determination model is implemented in the form of a regression, the output unit may output a non-standardized lens size. Unlike the standardized lens size, the non-standardized lens size may not refer to any one selected from a predetermined category but may refer to a numerical value of a lens size. The output unit may output the numerical value of the lens size. This will be described in detail in Content 3.3.

Figure 10:
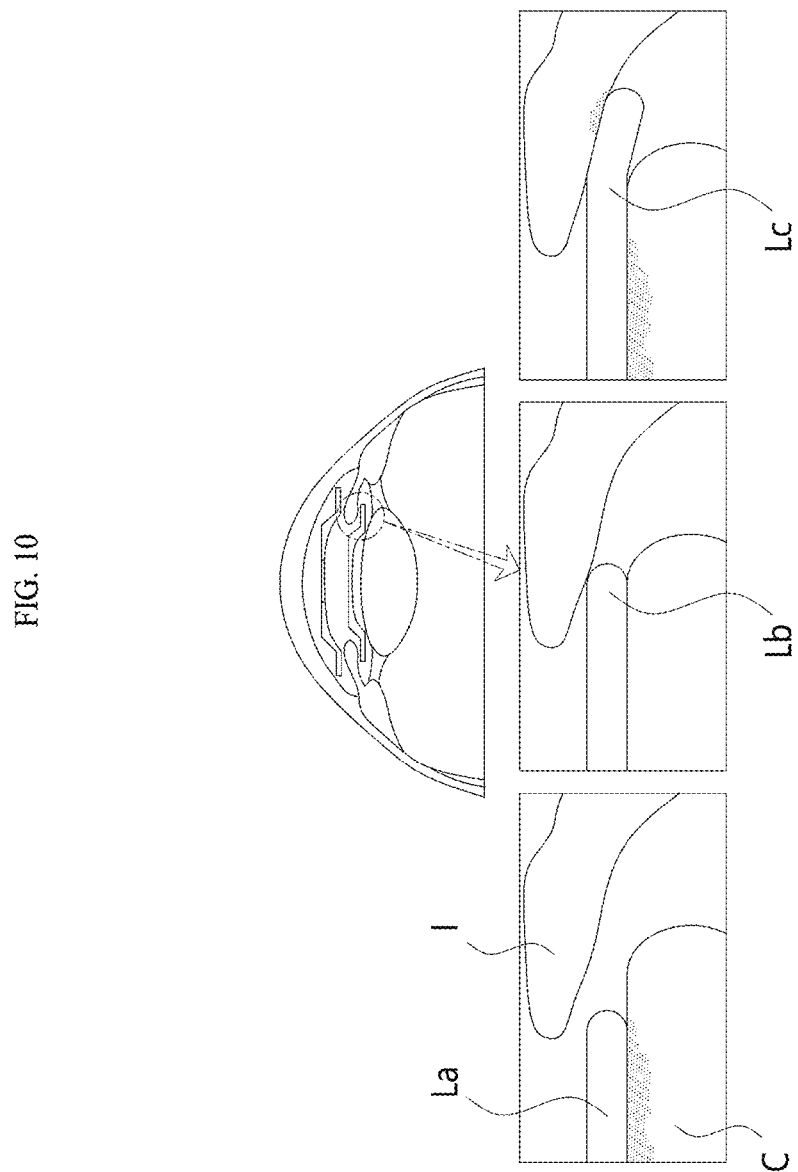
FIG. 10 shows diagrams for describing side effects of lens implant surgery according to an embodiment.

FIG. 10 shows diagrams for describing side effects of lens implant surgery. Referring to FIG. 10, left and right of FIG. 10 illustrate that a lens having an unsuitable lens size is inserted after lens implant surgery, and center of FIG. 10 illustrates that a lens having a suitable lens size is inserted during lens implant surgery. In addition, I represents an iris, La, Lb, and Lc represent a lens inserted into an eyeball, and C represents a crystalline lens.

The side effects of the lens implant surgery may occur when surgery is performed using a lens having an unsuitable lens size without considering characteristics of an eyeball of a person to be operated on. For example, referring to left of FIG. 10, the lens La having a certain lens size may be inserted into an eyeball of a person to be operated on. In this case, a lens having a small lens size is selected and inserted without considering characteristics of the eyeball of the person to be operated on, and thus, friction is generated between the lens and the crystalline lens to cause damage to the crystalline lens, thereby causing a cataract. In addition, referring to right of FIG. 10, the lens Lc having a certain lens size may be inserted into an eyeball of a person to be operated on. In this case, a lens having a large lens size is selected and inserted without considering characteristics of the eyeball of the person to be operated on, and thus, an end portion of the lens LC having a certain lens size is sandwiched between the crystalline lens and the iris to block a flow of a hydatoid, thereby causing glaucoma.

Therefore, in the lens implant surgery, a lens size, in which the possibility of occurrence of side effects is minimized, should be determined in consideration of characteristics of an eyeball of a person to be operated on. As an embodiment, referring to center of FIG. 10, the lens Lb having a certain lens size may be determined in consideration of characteristics of an eyeball of a person who is to be operated on and may have a lens size suitable for the eyeball of the person to be operated on. The lens Lb may have a size that does not cause friction between the lens Lb and the crystalline lens C, may be inserted at a position at which an appropriate distance between the lens LB and the iris is maintained, and may have a lens size by which the possibility of occurrence of side effects is minimized.

As described above, in consideration of characteristics of an eyeball of a person to be operated, only when a lens having a lens size in consideration of sizes of a lens inserted into the eyeball, a crystalline lens, an iris, and a lens insertion space is inserted, can the possibility of occurrence of side effects be minimized.

3.2. Lens Size Determination Process

Figure 11:
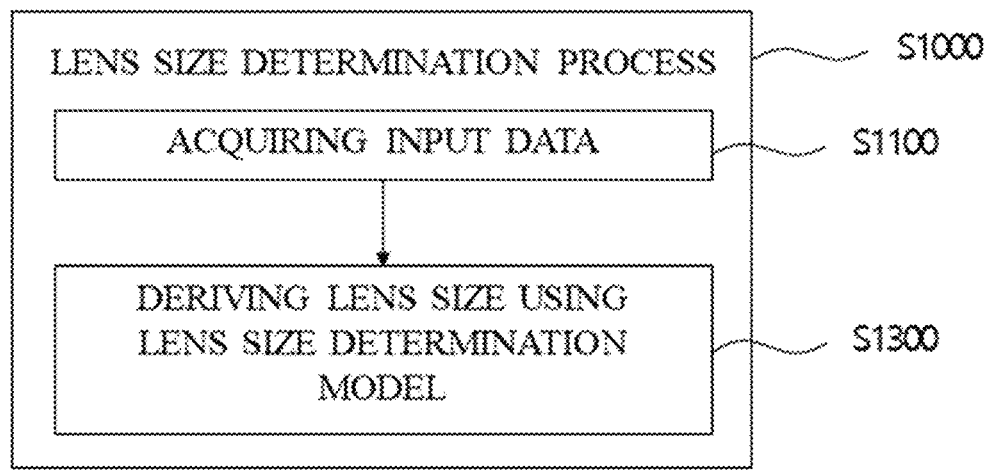
FIG. 11 is a diagram of a lens size determination process according to an embodiment.

FIG. 11 is a flowchart illustrating a lens size determination process S1000. Referring to FIG. 11, the lens size determination process S1000 may include acquiring input data such as a plurality of examination data of a person to be operated on (S1100) and deriving a lens size using a lens size determination model (S1300). The lens size determination process S1000 may be performed by the lens size determination module 1000 described above with reference to FIG. 2.

Specifically, in operation S1100 of acquiring the input data, the input data may include a plurality of examination data acquired from a plurality of examination apparatuses related to measurement of an eyeball of the person to be operated on. In an embodiment, the plurality of examination apparatuses related to the measurement of the eyeball may be examination apparatuses that perform measurement using a laser and/or high-frequency ultrasound. For example, the examination apparatuses may include an ultrasound biomicroscopy (UBM) apparatus, an optical coherence tomography (OCT) apparatus, and the like.

In an embodiment, the plurality of examination data may include the parameters described above with reference to FIG. 9. Specifically, the plurality of examination data may include parameters such as conical curvature, a refractive error (myopia, astigmatism, or farsightedness degree), a pupil size, an intraocular pressure, vision, a conical shape, a corneal thickness, an eyeball length, a lens insertion space, an ATA distance, an ACD-epi, an ACD-end, a CCT, a CLR, a WTW, an AL, a measured distance between irises, and the like.

A lens size may be derived from the acquired input data using a lens size determination model.

In addition, in an embodiment, since a degree of influence on a result value varies according to types of the parameter included in the input data, the result value may vary for each input data.

Furthermore, in another embodiment, each input data may include at least some of the same parameters, but the same parameters may be derived by different examination apparatuses. Even when the same parameters are derived from the different examination apparatuses, numerical values representing the same parameters may be different. The difference may occur due to methods and principles of measuring parameters being different for each examination apparatus. For example, a parameter A obtained from a UBM apparatus (wherein the parameter A represents an arbitrary parameter) is a parameter that performs the same function as a parameter A obtained from an OCT apparatus, but numerical values representing the parameters A may be different. As described above, since accuracies of measured parameters are different according to the examination apparatuses, input data may have different degrees of influence on a result value.

In addition, each parameter or even the same parameter may have a different degree of influence on a result value according to which examination apparatus outputs a parameter. Thus, a priority between input data may be changed.

In order to increase accuracy of a result value, a weight may be increased for a parameter with a high priority or a parameter derived from an examination apparatus with a high priority.

In an embodiment, the input data may include priority data. The priority data may be prioritized according to types of the parameters included in the input data. For example, when the input data includes a parameter having a large degree of influence on deriving a lens size, the input data may be a first priority data. When the input data includes a second parameter which has a smaller degree of influence on deriving a lens size as compared with the first parameter, the input data may be a second priority data. For convenience of description, only the first priority data and the second priority data have been described, but not limited thereto. The input data may include a plurality of priority data.

In an embodiment, when a lens size is determined using the input data including the first priority data, a first lens size may be derived, and when a lens size is determined using the input data including the second priority data, a second lens size may be derived. For example, a probability of accuracy of a result value in the first lens size may be higher than that of the second lens size. In this case, when surgery is performed on a person to be operated on using the first lens size, fewer side effects may occur as compared with when surgery is performed using the second lens size.

In an embodiment, in operation S1300 of deriving the lens size, when the input data does not include the first priority data and does include the second priority data, the lens size determination unit may derive the lens size using the second priority data.

In an embodiment, the input data may necessarily include the first priority data. This is to ensure accuracy of a result value.

In the training operation S100, the lens size determination model may learn the first priority data and the second priority data together or separately. According to an embodiment, when the first priority data and the second priority data are learned together, in operation S1300 of deriving the lens size, any one of the first priority data and the second priority data may be used. According to another embodiment, when only the first priority data is learned, in operation S1300 of deriving the lens size, only the first priority data may be used. When only the second priority data is learned, in operation S1300 of deriving the lens size, only the second priority data may be used. Of course, not limited thereto, and according to an embodiment, even when only the first priority data is learned, in operation S1300 of deriving the lens size, the second priority data may be used, and even when only the second priority data is learned, in operation S1300 of deriving the lens size, the first priority data may be used.

3.3. Embodiments

Figure 12:
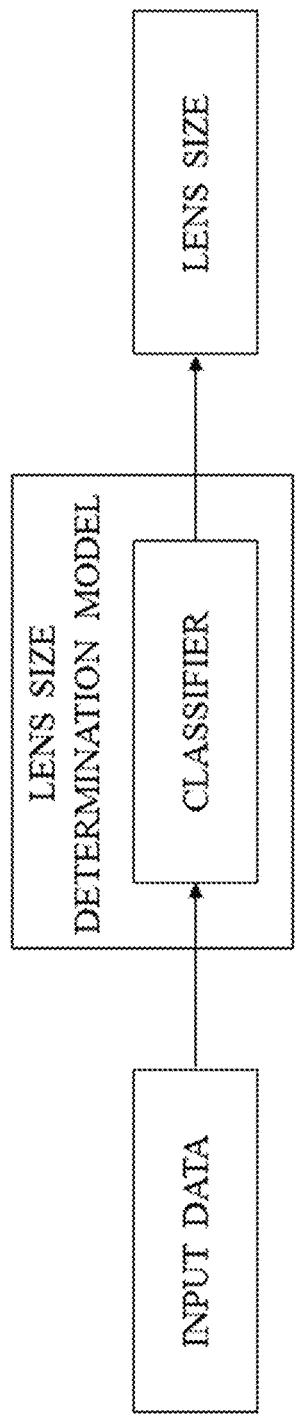
FIG. 12 is a diagram illustrating the determination of a lens size according to an embodiment.
Figure 13:
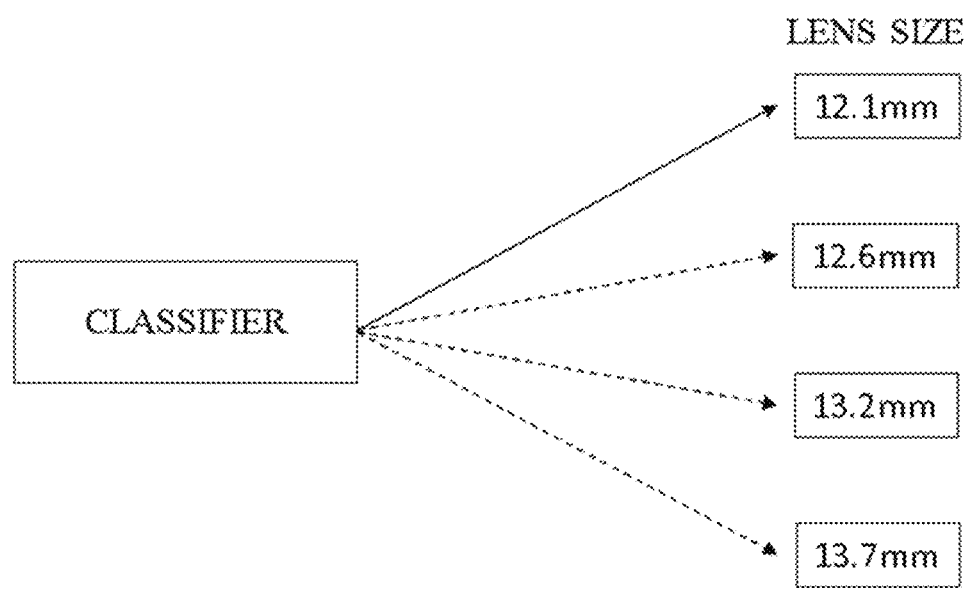
FIG. 13 is a diagram illustrating the determination of the lens size according to an embodiment.

FIGS. 12 and 13 are diagrams illustrating the determination of a lens size according to an embodiment. That is, in FIGS. 12 and 13, operation S1300 described above with reference to FIG. 11 will be described in more detail. Referring to FIGS. 12 and 13, in an embodiment, the lens size determination model may be implemented to include a classifier.

In an embodiment, the classifier may use a type of algorithm such as a decision tree, a support vector machine, or a random forest. This is merely an example, and not limited thereto.

In an embodiment, the lens size determination module 1000 may input an input data to the lens size determination model 110 and may derive a lens size from the lens size determination model 110. The lens size determination model 110 may include the classifier, and the classifier may determine any one of lens sizes having preset values.

In addition, a standardized lens size may be obtained from an input .data of a person to be operated on using the lens size determination model implemented to include the classifier. The classifier may determine one lens size of a lens to be inserted into an eyeball of the person to be operated on from the input data of the person to be operated on.

In addition, the standardized lens size may be an existing lens size. The existing lens size may be a size that is predetermined according to a preset standard. In an embodiment, a standardized lens size, for example, a lens size of 12.6 mm, which is one of sizes of 12.1 mm, 12.6 mm, 13.2 mm, and 13.7 mm, may be determined from the input data of the person to be operated on by using the lens size determination model implemented to include the classifier.

Figure 14:
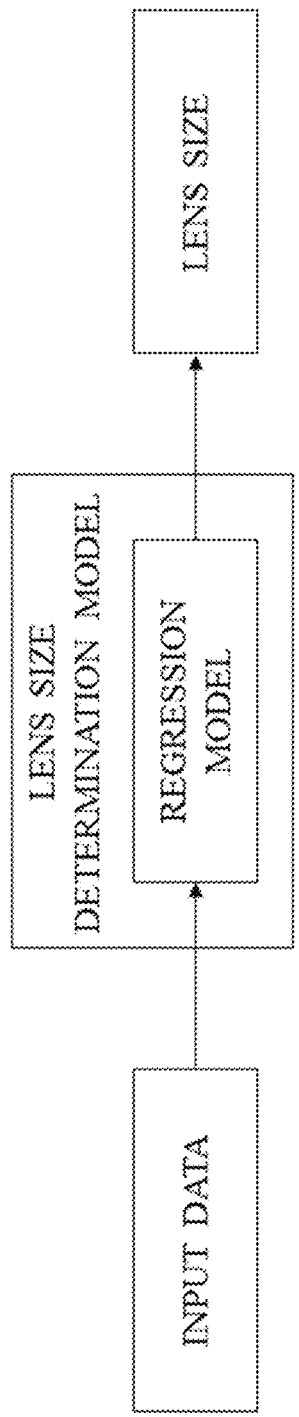
FIG. 14 is a diagram illustrating the determination of a lens size according to another embodiment.
Figure 15:
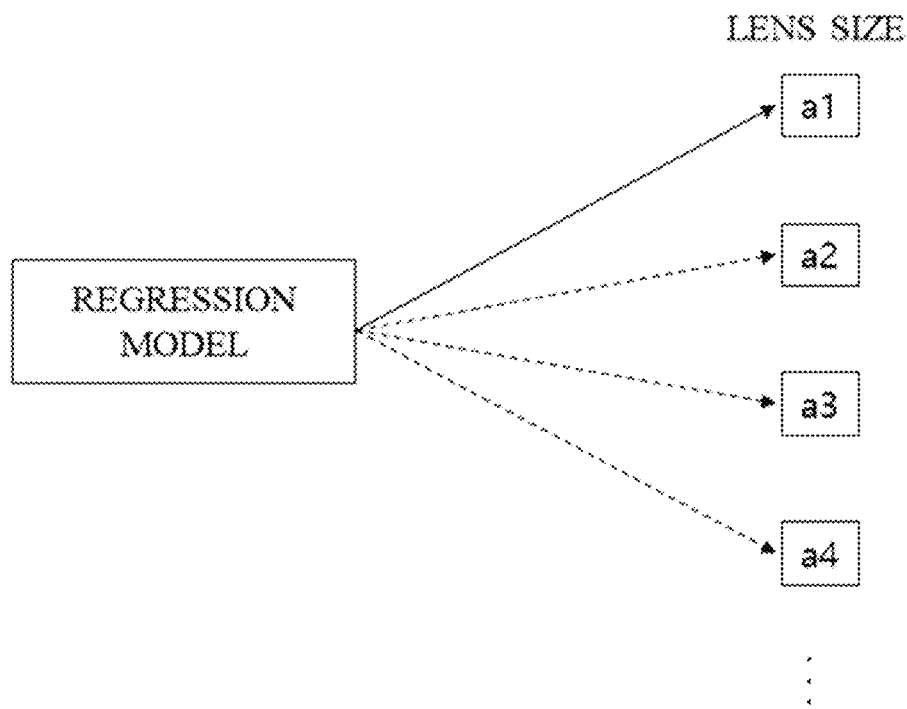
FIG. 15 is a diagram illustrating the determination of the lens size according to another embodiment.

FIGS. 14 and 15 are diagrams illustrating the determination of a lens size according to another embodiment. That is, in FIGS. 14 and 15, operation S1300 described above with reference to FIG. 11 will be described in more detail. Referring to FIGS. 14 and 15, in an embodiment, the lens size determination model may be implemented to include a regression.

In an embodiment, the regression may use a type of algorithm such as a linear regression, a regression tree, a support vector regression, or a kernel regression. This is merely an example, and not limited thereto.

In an embodiment, the lens size determination module 1000 may input an input data to the lens size determination model 110 and may derive a lens size from the lens size determination model 110. The lens size determination model 110 may include the regression, and the regression may determine any one of lens sizes that may or may not have preset values.

In addition, a standardized and/or non-standardized lens size may be obtained from an input data of a person to be operated on using the lens size determination model implemented to include the regression. The regression may derive a probability with respect to lens sizes of a lens to be inserted into an eyeball of the person to be operated from the input data of the person to be operated on. A lens size derived at the highest probability may be the most suitable lens size among the lens sizes of the lens to be inserted into the eyeball of the person to be operated on.

According to an embodiment, the output unit 1500 may output a non-standardized lens size according to a learning method of the lens size determination model. The non-standardized lens size may be expressed as all lens sizes including an existing lens size. Specifically, the non-standardized lens size is a size of a lens to be inserted into the eyeball in consideration of characteristics of the eyeball of the person to be operated on and may be larger or smaller than an existing lens size or may be a size between the existing lens sizes. The non-standardized lens size may be a lens size of a lens to be custom-made in consideration of the characteristics of the eyeball of the person to be operated on. The non-standardized lens size may be a lens size more optimized for the eyeball of the person to be operated on as compared with a standardized lens size. The non-standardized lens size may be a lens size customized to the eyeball of the person to be operated on.

In another embodiment, the lens size determination model 110 may be implemented to include a classifier and a regression. That is, the lens size determination model 110 may be implemented by combining the classifier and the regression in series or in parallel. As an example, the lens size determination module 1000 inputs an input data into the lens size determination model 110 in which the classifier and the regression are combined and may derive lens sizes and numerical values from the combined lens size determination model 110. For example, a standardized lens size of 12.6 mm through the classifier may be derived from a lens size of 12.5 mm output through the regression. Alternatively, a non-standardized lens size of 13.3 mm through the regression may be derived from a lens size of 13.2 mm output through the classifier. This is merely an example, and the lens size output through the classifier and the lens size output through the regression may be simultaneously derived.

Figure 16:
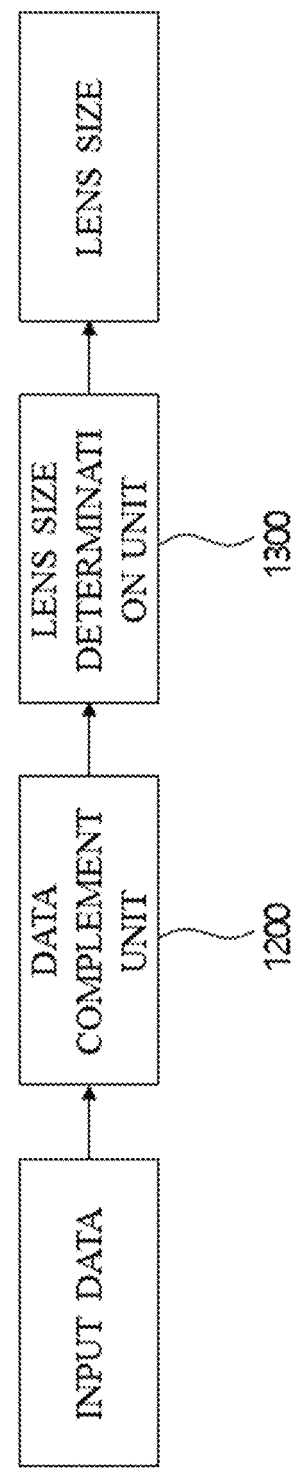
FIG. 16 is a diagram illustrating the determination of a lens size according to still another embodiment.

FIG. 16 is a diagram illustrating the determination of a lens size according to still another embodiment. Referring to FIG. 16, the lens size determination module 1000 may further include a data complement unit 1200 which supplements an input data.

When priority data may not be acquired from an examination apparatus, or in an environment in which an examination apparatus capable of acquiring priority data is not provided, the data complement unit 1200 may derive a more accurate lens size with respect to a lens size of a lens to be inserted into an eyeball of a person to be operated on during lens implant surgery.

According to an embodiment, the input data may include a first priority data and a second priority data, may include only the first priority data, and may include only the second priority data. When a user may use only the second priority data and may not use the first priority data as the input data, accuracy of a result value may be lower as compared with when only the first priority data is used. As in this case, even when the first priority data is missing, in order to improve accuracy of a result value, the first priority data may be estimated using the data complement unit 1200.

The data complement unit 1200 may estimate the first priority data from input data.

The priority data may include parameters having a large degree of influence on a result value. In order to increase accuracy of a result value, data with a high priority, that is, data which includes parameters having a large degree of influence on a result value, may be input. For example, when the lens size determination unit determines a lens size using a first input data including an ATA distance among parameters, accuracy of a result value may be high. When a lens size is determined using a second input data including only a CCT without an ATA distance, accuracy of a result value may be low. In this case, the first input data may include the first priority data having a high priority, and the accuracy of the result value may be high.

According to circumstances, even when the first priority data may not be acquired and only the second priority data may be acquired, in order to increase accuracy, the data complement unit may estimate the first priority data using the second input data. The estimated first priority data may be used as an input data in the lens size determination unit 1300. For example, an ATA distance corresponding to a missing value may be estimated from parameters such as a CCT and vision data included in the second input data.

In an embodiment, when an examination apparatus capable of measuring the first priority data is not provided, the first priority data may be estimated using the data complement unit.

In an embodiment, the data complement unit 1200 may estimate an input data other than the first priority data as the first priority data using a separate formula.

In an embodiment, the data complement unit 1200 may estimate an input data other than the first priority data as the first priority data using a separate formula through a data complement model. Although not shown, the data complement model may be trained based on the first priority data and the second priority data as learning data. As an example, the data complement model may be trained to derive the first priority data by receiving the second priority data. When the second priority data is input as input data, the trained data complement model may derive the estimated first priority data. This is merely an example, and not limited thereto.

In addition, in an embodiment, the lens size determination model may use multiple machine learning algorithms together among a plurality of machine learning algorithms for calculating a predicted value. As an example, the lens size determination model may be trained using an ensemble method and may estimate a lens size. Since the ensemble method is used in the lens size determination model, accuracy of the lens size determination model may be improved.

Figure 17:
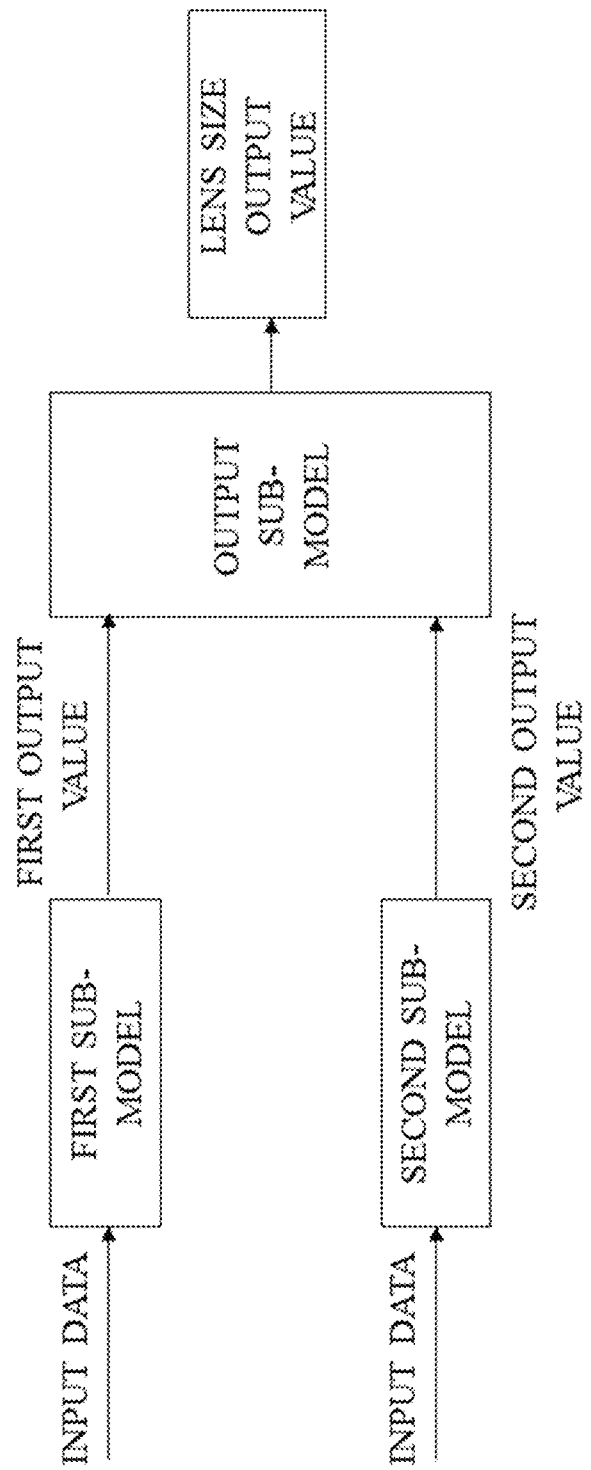
FIG. 17 is a schematic diagram illustrating a plurality of sub-models of a lens size determination model.

FIG. 17 is a schematic diagram illustrating a plurality of sub-models of the lens size determination model. Referring to FIG. 17, the lens size determination model may include the plurality of sub-models. The plurality of sub-models may each independently determine a lens size. For example, a first sub-model may be a model that is trained using a random forest method to determine a lens size, and a second sub-model may be a model that is trained using a decision tree method to determine a lens size. In addition, although only the first sub-model and the second sub-model are illustrated in FIG. 17, this is merely an example, and the sub-models may be provided with a plurality of sub-models.

The plurality of sub-models may be connected in parallel. Here, input data inputted to the plurality of sub-models and output values outputted from the plurality of sub-models may be the same or different.

The lens size determination model may output a prediction result based on the output value of the sub-model.

The lens size determination model may include an output sub-model that outputs a prediction result based on the output values of the plurality of sub-models connected in parallel. In an embodiment, when a first output value and a second output value, which are output values of the first sub-model and the second sub-model, are the same value, the output sub-model may output the same value. In another embodiment, when the first output value and the second output value, which are the output values of the first sub-model and the second sub-model, are different, the output sub-model may consider the output values of the plurality of sub-models at a certain ratio to output a prediction result or may output a specific value among a plurality of output values. In other words, the output sub-model may give weights to the first output value from the first sub-model and the second output value from the second sub-model and may output a lens size by reflecting the weights applied to the output values. For example, when a weight of 0.8 is given to the first output value, a weight of 0.2 is given to the second output value, the first output value represents 12.6 mm among standardized lens sizes, and the second output value represents 13.2 mm among the standardized lens sizes, the output sub-model may derive a lens size of 12.6 mm, which is the first output value having a high weight, as an output value.

In addition, for example, when a weight of 0.8 is given to the first output value, a weight of 0.2 is given to the second output value, the first output value represents 12.6 mm among non-standardized lens sizes, and the second output value represents 13.2 mm among the non-standardized lens sizes, the output sub-model may derive a lens size of 12.7 mm, to which a weight is reflected, as an output value.

In addition, the weight may be determined in a training process. That is, the training operation S100 described above with reference to FIG. 8 may be performed on the lens size determination model including the plurality of sub-models, and the weight may be determined in the training operation S100.

In another embodiment, the output sub-model may output another value generated based on the plurality of output values as a prediction result. Here, the output value of the output sub-model may be the same type as or different type from the plurality of output values.

In an embodiment, the first sub-model and the second sub-model may be the same, and input data inputted to the sub-models may be different. The input data may be a first priority data or a second priority data. A high weight may be given to the sub-model to which data with a high priority is inputted. For example, a higher weight may be given to the first sub-model to which the first priority data is input as compared with the second sub-model to which the second priority data is input, thereby deriving the first output value as a lens size output value.

4. PREDICTION OF VAULTING VALUE

4.1. Definition of Vaulting Value

Figure 18:
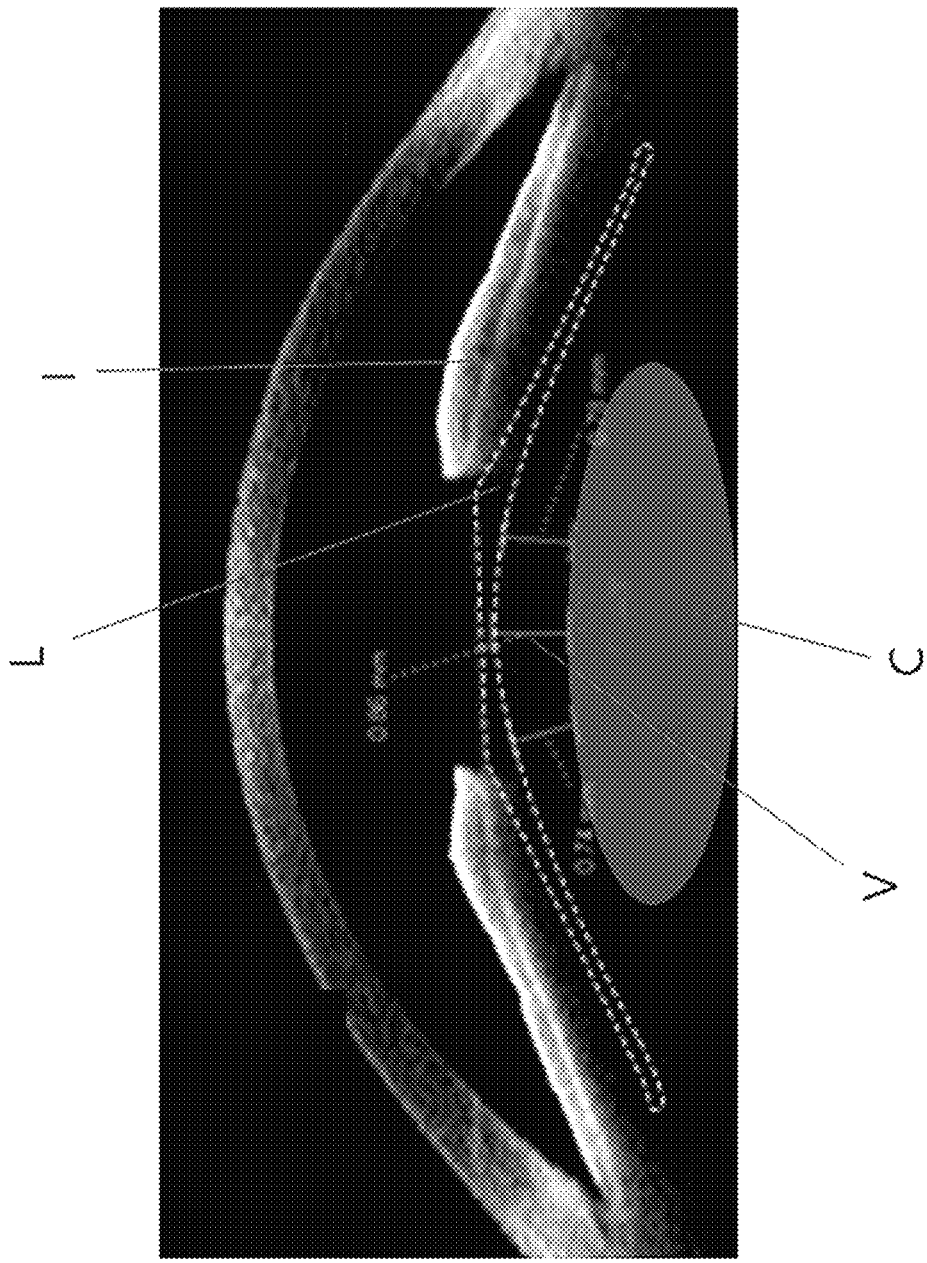
FIG. 18 is a diagram for defining a vaulting value.

FIG. 18 is a diagram for defining a vaulting value. The vaulting value (also referred to as a vault value) is a value representing a distance between a rear surface of a lens to be inserted into an eyeball of a person to be operated on with lens implant surgery and an anterior surface of a crystalline lens. Specifically, the vaulting value is defined as the shortest distance of a plurality of distances between the rear surface of the lens to be inserted into the eyeball and the anterior surface of the crystalline lens. Referring to FIG. 18, L represents a lens inserted into an eyeball of a person to be operated on, I represents an iris, C represents a crystalline lens, and V represents a vaulting value. The lens L may be inserted into a space between the iris I and the crystalline lens C. A plurality of distances may exist between the lens inserted into the eyeball and the anterior surface of the crystalline lens. Among the plurality of distances, the shortest distance between the rear surface of the lens and the anterior surface of the crystalline lens, that is, a distance between the lens and the crystalline lens in a vertical direction from a center of a cornea, may correspond to the vaulting value V.

In general, a vaulting value may be measured after lens implant surgery in order to check whether a lens having a suitable size is inserted into an eyeball of a patient. When the vaulting value measured after the surgery is included within a certain range, it may be determined that a lens size of the lens inserted into the eyeball is a lens size suitable for the eyeball of the patient. As an example, a vaulting value may be included in a certain range of 250 μm to 750 μm. In an embodiment, when the vaulting value is 250 μm or less, the lens inserted into the eyeball of the patient may be regarded as having a size smaller than a size suitable for the eyeball of the patient. When a lens having a size smaller than a lens size suitable for the eyeball of the patient is inserted, a cataract may be caused as described with reference to left of FIG. 10. In another embodiment, when the vaulting value is 750 μm or more, the lens inserted into the eyeball of the patient may be regarded as having a size larger than a size suitable for the eyeball of the patient. When a lens having a size larger than a lens size suitable for the eyeball of the patient is inserted, glaucoma may be caused as described with reference to right of FIG. 10. Therefore, in order to prevent side effects of lens implant surgery, the vaulting value after the surgery may need to be included within an appropriate range. That is, there is a need to accurately design and then insert a lens before lens implant surgery. Hereinafter, a vaulting value prediction module for predicting a vaulting value and a vaulting value prediction process will be described.

4.2. Configuration of Vaulting Value Prediction Module

Figure 19:
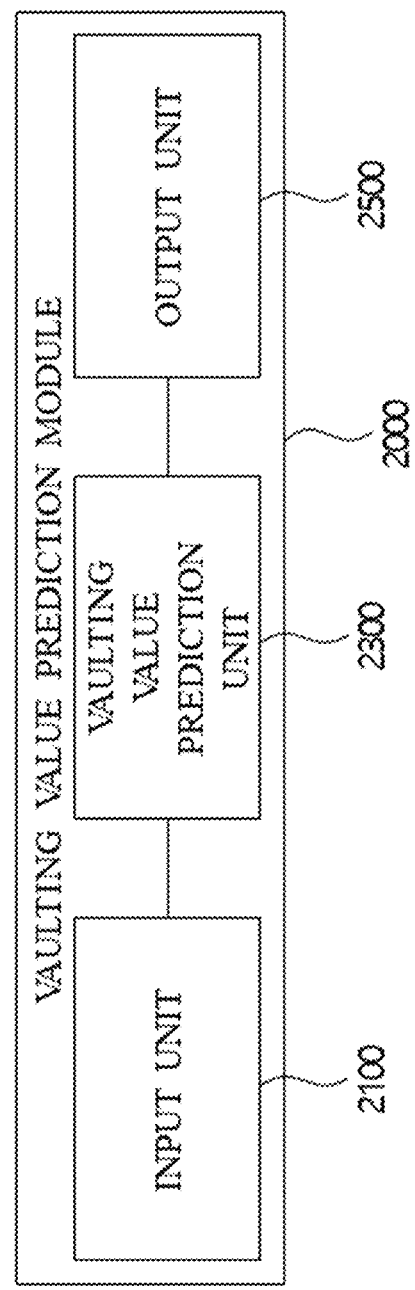
FIG. 19 is a diagram illustrating a vaulting value prediction module according to an embodiment.

FIG. 19 is a diagram illustrating a configuration of the vaulting value prediction module 2000. In an embodiment, the vaulting value prediction module 2000 may output a prediction vaulting value in an eyeball of a person to be operated on from an input data.

Referring to FIG. 19, the vaulting value prediction module 2000 may include an input unit 2100, a vaulting value prediction unit 2300, and an output unit 2500.

The input unit 2100 may acquire an input data from a database. The input data may include a plurality of examination data of the person to be operated on.

Specifically, the input unit 2100 may be connected directly to the database to acquire the input data. In addition, the input unit 2100 may receive and acquire the input data from a server or other external devices.

The input data may include the examination data of the person to be operated on. The examination data may be the same as that described in Content 3.1 above. Hereinafter, only different contents will be described.

According to an embodiment, the input data may include an arbitrary expected lens size of a lens to be inserted into the eyeball of the person to be operated on. The arbitrary expected lens size may be a standardized or non-standardized lens size.

In an embodiment, the vaulting value prediction unit 2300 may predict a vaulting value of the person to be operated on from the input data.

In addition, when the predicted vaulting value is included within a certain range, the vaulting value prediction unit 2300 may provide the predicted vaulting value, and a user may determine that surgery has been performed using a suitable lens size based on the predicted vaulting value.

In an embodiment, the vaulting value prediction unit 2300 may provide information about whether lens implant surgery of the person to be operated on is possible using an input lens size according to the predicted vaulting value. For example, when the predicted vaulting value is derived as 200 μm, which is not included within a range of 250 μm to 750 μm, the vaulting value prediction unit 2300 may determine that lens implant surgery of the person to be operated on is impossible. This is merely an example, and not limited thereto, and to the contrary, when the predicted vaulting value is included within a certain range, the vaulting value prediction unit 2300 may determine that lens implant surgery is possible.

In addition, the vaulting value prediction unit 2300 may provide information about whether the input lens size is suitable for lens implant surgery of the person to be operated on according to the predicted vaulting value. For example, when the predicted vaulting value is 500 μm, the vaulting value prediction unit 2300 may provide information indicating that a lens size of 13.2 mm inputted as an input data is suitable for the lens implant surgery of the person to be operated on. In addition, when the predicted vaulting value is 800 μm, the vaulting value prediction unit 2300 may provide information indicating that a lens size of 13.2 mm inputted as an input data is not suitable for the lens implant surgery of the person to be operated on. This is merely an example, and not limited thereto.

Specific operations of the vaulting value prediction unit 2300 will be described in more detail with reference to FIG. 20.

The output unit 2500 may output a vaulting value obtained through the vaulting value prediction unit 2300 to a user. In an embodiment, the output unit 2500 may provide a display that visually outputs output data on a screen. In addition, the output unit 2500 may output various forms such as an image and a text.

In an embodiment, the predicted vaulting value may be a criterion for determining a result of lens implant surgery. For example, when the predicted vaulting value is included within a range of 250 µm to 750 µm, the user may determine that surgery has been performed using a lens size suitable for the eyeball of the person to be operated on.

In an embodiment, according to a result value of the vaulting value prediction unit 2300, it is possible to output information about whether lens implant surgery of a person to be operated on is suitable or available using a lens size input as input data.

4.3. Vaulting Value Prediction Process

Figure 20:
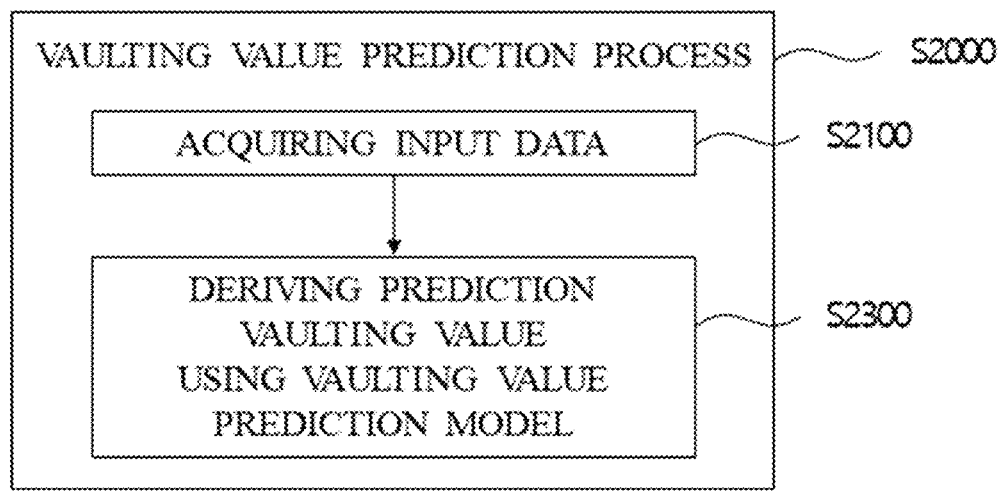
FIG. 20 is a diagram of a vaulting value prediction process according to an embodiment.

FIG. 20 is a flowchart of a vaulting value prediction process S2000. Referring to FIG. 20, the vaulting value prediction process S2000 includes acquiring an input data such as examination data of a person to be operated on (S2100) and deriving a prediction vaulting value using the vaulting value prediction model (S2300). The vaulting value prediction process S2000 may be performed by the vaulting value prediction module 2000 described above with reference to FIG. 2.

Specifically, in operation S2100 of acquiring the input data, the input data may include a plurality of examination data acquired from a plurality of examination apparatuses related to measurement of an eyeball of the person to be operated on. This is the same as that of the lens size determination process in Content 3.2 and thus is omitted.

In an embodiment, the input data may include the plurality of examination data and arbitrary lens sizes.

In operation S2300 of deriving the prediction vaulting value, a vaulting value corresponding to the arbitrary lens size may be predicted using the vaulting value prediction model based on the plurality of examination data of the person to be operated on.

In an embodiment, as described with reference to FIG. 3, the vaulting value prediction model 120 may be trained by the training device 11 and may derive a vaulting value predicted by the determination assistance device 21. In addition, the vaulting value prediction model 120 may be trained through the training operation S100 and may derive a predicted vaulting value through the determining operation S200. The matters described with reference to FIGS. 3 and 8 may be applied unchanged to the vaulting value prediction model 120.

4.4. Embodiments

In an embodiment, the vaulting value prediction module may predict a vaulting value using a plurality of examination data and/or expected lens sizes of a person to be operated on as an input data.

Figure 21:
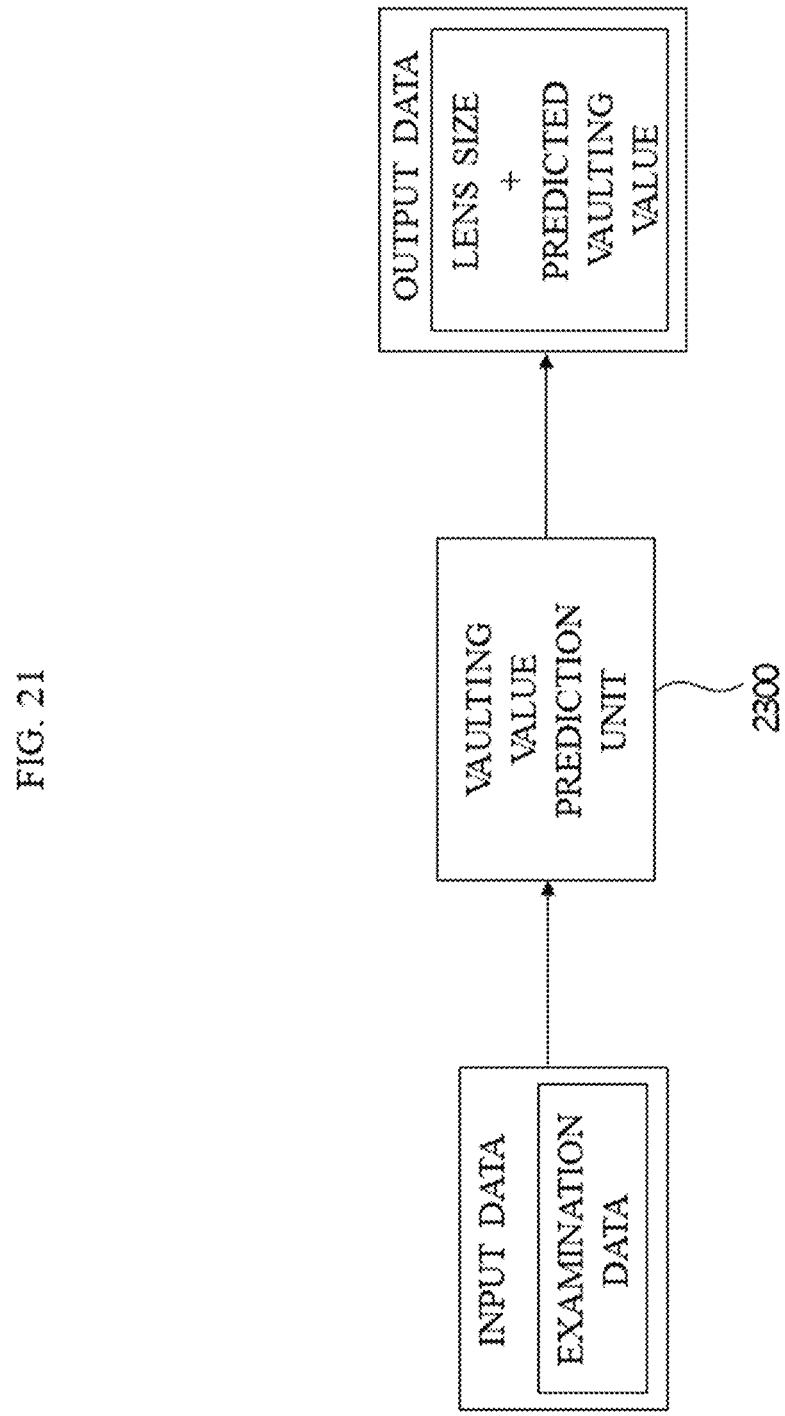
FIG. 21 is a diagram illustrating the prediction of a vaulting value according to an embodiment.

FIG. 21 is a diagram illustrating the prediction of a vaulting value according to an embodiment. Referring to FIG. 21, the vaulting value prediction unit 2300 may predict a vaulting value and a lens size using a plurality of examination data of a person to be operated on as an input data.

The vaulting value may be derived differently according to a size of a lens to be inserted into an eyeball.

In an embodiment, when the examination data is input to the vaulting value prediction model 120, the vaulting value prediction module 2000 may output a lens size and a predicted vaulting value together. When the lens size and the predicted vaulting value are output together as output data, a user may accurately determine a lens size suitable for characteristics of an eyeball of a person to be operated on based on the predicted vaulting value. For example, when a lens size of 12.6 mm and a predicted vaulting value of 500 µm are output, since the predicted vaulting value is included within an appropriate range, the user may determine that the output lens size is a lens size suitable for the characteristics of the eyeball of the person to be operated on. Alternatively, when a lens size of 13.2 mm and a predicted vaulting value of 900 µm are output, since the predicted vaulting value is not included within an appropriate range, the user may determine that the output lens size is a lens size not suitable for the characteristics of the eyeball of the person to be operated on. This is merely an example, and not limited thereto.

In an embodiment, the vaulting value prediction model 120 may be trained using learning data for inputting examination data and outputting a vaulting value and a lens size. The training operation S100 described with reference to FIG. 8 may be applied unchanged to a training operation of the vaulting value prediction model intact.

In an embodiment, a predicted vaulting value may be a vaulting value within a certain range. That is, the output unit 2500 may output a vaulting value within a certain range and a lens size corresponding thereto. For example, when a vaulting value is 500 µm which is within a range of 250 µm to 750 µm, the output unit 2500 may output a lens size of 12.6 mm.

Figure 22:
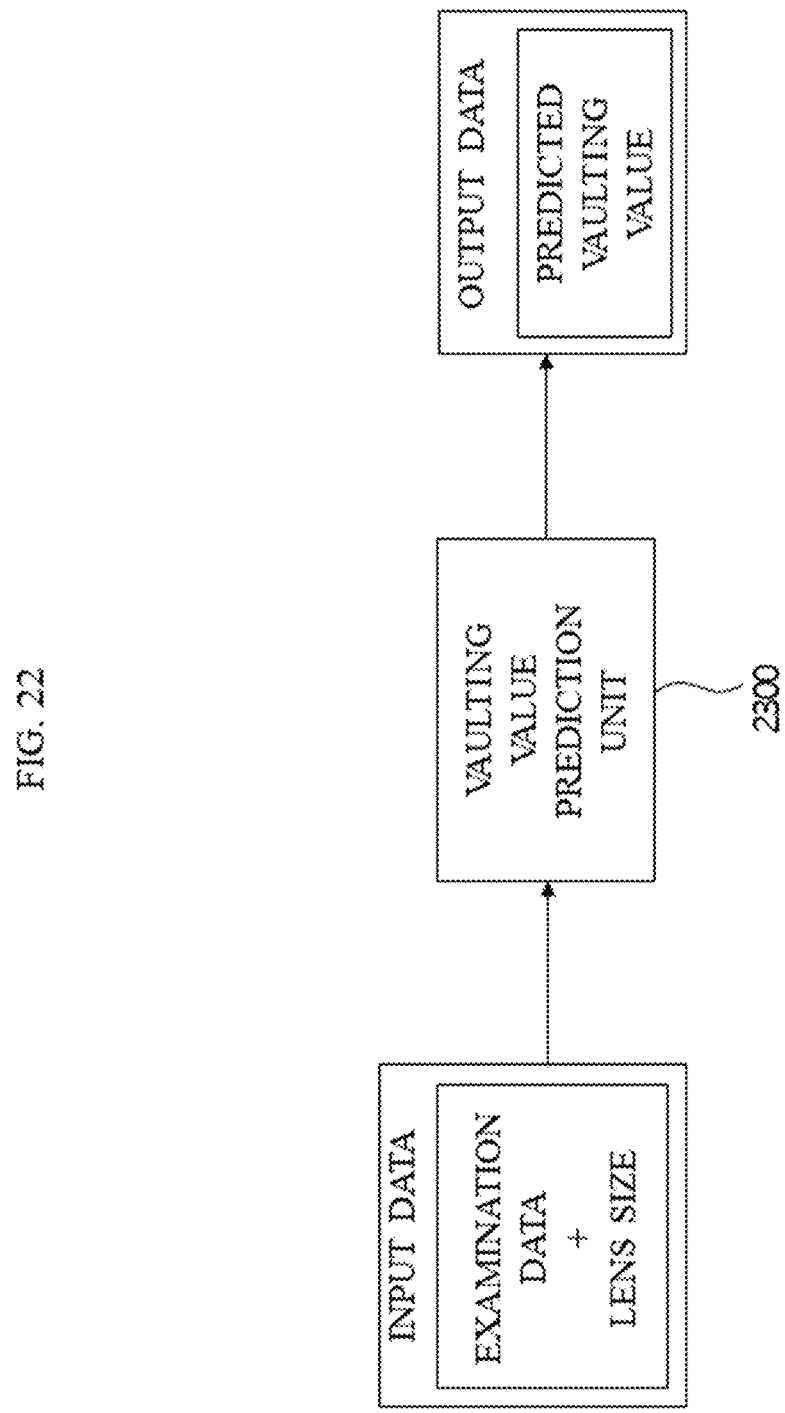
FIG. 22 is a diagram illustrating the prediction of a vaulting value according to another embodiment.

FIG. 22 is a diagram illustrating the prediction of a vaulting value according to another embodiment. Referring to FIG. 22, the vaulting value prediction unit 2300 may predict a vaulting value using a plurality of examination data and arbitrary lens sizes of a person to be operated on as an input data.

In an embodiment, when the examination data and the arbitrary lens size are inputted to the vaulting value prediction model 120, the vaulting value prediction module 2000 may output a predicted vaulting value. A user may determine whether the input arbitrary lens size is suitable for characteristics of an eyeball of the person to be operated on based on the predicted vaulting value. For example, after the examination data and a lens size of 13.2 mm are input as an input data, when a predicted vaulting value of 450 µm is output, it may be determined that the lens size of 13.2 mm, which is the arbitrary lens size, is suitable for the characteristics of the eyeball of the person to be operated on. This is merely an example, and not limited thereto.

In an embodiment, the vaulting value prediction model 120 may be trained using learning data for inputting examination data and a lens size and outputting a vaulting value. The training operation S100 described with reference to FIG. 8 may be applied unchanged to a training operation of the vaulting value prediction model.

Although not shown, in an embodiment, the vaulting value prediction unit 2300 may be implemented to interwork with the lens size determination unit 1300. In this case, a user may verify accuracy of a result value derived through the lens size determination unit 1300. For example, when a lens size of 13.2 mm derived through the lens size determination unit 1300 is inputted as an input data of the vaulting value prediction unit 2300 together with examination data and when a predicted vaulting value is 500 µm, since the vaulting value is included within a certain range, it can be verified that the lens size of 13.2 mm, which is a result value of the lens size determination unit, is a result value suitable for the eyeball of the person to be operated on and accuracy of the result value is also high.

In an embodiment, the lens size determination unit 1300 and the vaulting value prediction unit 2300 may be connected in series. Specifically, a lens size (output data) derived using the lens size determination unit 1300 may be acquired as an input data of the vaulting value prediction unit 2300. That is, a lens size, which is a result value of the lens size determination unit, and a plurality of examination data of a person to be operated on may be inputted as the input data of the vaulting value prediction unit 2300. Therefore, the vaulting value prediction unit 2300 may output a prediction vaulting value corresponding to an input lens size.

5. DETERMINATION OF LENS POWER

5.1. Configuration of Lens Power Determination Module

Even when the maximum corrected vision of a surgery eye is greater than or equal to a target vision after lens implant surgery, quality of vision may be degraded due to residual astigmatism after surgery. For example, even when, after the lens implant surgery, the corrected vision of the surgery eye reaches a target vision of 1.2 and astigmatism is partially corrected, residual astigmatism may remain. In this case, a patient may not obtain an expected surgical result due to the residual astigmatism. Therefore, when a power of a lens used for lens implant surgery is determined, factors of astigmatism such as corneal astigmatism may need to be considered.

In an embodiment, when a power of a lens is determined, it is necessary to determine the power of the lens in consideration of not only the maximum corrected vision, but also corneal astigmatism caused by surgery. In this case, the residual astigmatism is predicted in advance, and an element for correcting the residual astigmatism may be reflected in the lens in advance. Accordingly, a user can obtain not only a target vision but also a desired quality of vision.

Figure 23:
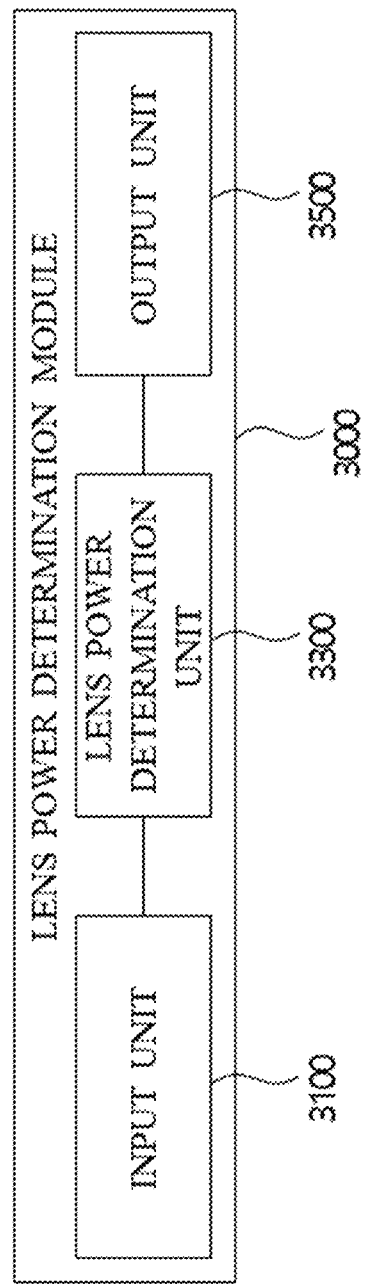
FIG. 23 is a diagram of a lens power determination module according to an embodiment.

FIG. 23 is a diagram illustrating a configuration of the lens power determination module 3000. In an embodiment, the lens power determination module 3000 may output a power of a lens to be inserted into an eyeball of a person to be operated on from input data.

Referring to FIG. 23, the lens power determination module 3000 may include an input unit 3100, a lens power determination unit 3300, and an output unit 3500.

The input unit 3100 may acquire an input data from a database. The input data may include a plurality of examination data of the person to be operated on.

Specifically, the input unit 3100 may be connected directly to the database to acquire the input data. In addition, the input unit 3100 may receive and acquire the input data from a server or other external devices.

The input data may include the examination data of the person to be operated on. The examination data may be the same as that described in Content 3.1 above. Hereinafter, only different contents will be described.

According to an embodiment, the examination data may include measured uncorrected vision of the person to be operated, a diopter measured from an eyeball, an astigmatic axis, parameters of a cylindrical orientation, corneal astigmatism, lenticular astigmatism, data about a ratio of myopia and astigmatism, and the like.

According to an embodiment, the input data may include corneal incision information. The corneal incision information may mean information about a predicted or planned corneal incision in a cornea incision process of the person to be operated on before a lens is inserted during lens implant surgery. In the corneal incision process of the lens implant surgery of the person to be operated on, the corneal incision information may include a corneal incision method, a corneal incision location, a corneal incision direction, and/or a corneal incision degree. An amount of change in astigmatism may vary according to the corneal incision location of the corneal incision information, and an astigmatism (SIA) value caused by surgery may vary according to a corneal incision size. Therefore, at the time of determining a lens power, when the lens power is determined after astigmatism, in which factors such as an amount of change in astigmatism and/or astigmatism caused by surgery are adjusted, is predicted in consideration of the conical incision information, it is possible to obtain an effect of further improving quality of vision.

In an embodiment, the lens power determination unit 3300 may determine a lens power suitable for the eyeball of the person to be operated on by applying an input data such as a plurality of examination data of the person to be operated on to the lens power determination model 130. Here, the suitable lens power may mean a lens power in which the possibility of occurrence of side effects is minimized when lens implant surgery is performed on the person to be operated on, and quality of vision is high. As side effects in the determination of the lens power, there may be decreased vision and headaches according to the decreased vision.

In an embodiment, in order to determine a suitable lens power, the lens power determination unit 3300 inputs an input data such as a plurality of examination data of the person to be operated on and expected corneal incision information of the person to be operated on, thereby outputting a lens power suitable for the eyeball of the person to be operated on.

Specific operations of the lens power determination unit 3300 will be described in more detail with reference to FIG. 24.

The output unit 3500 may output information (output data) about a power of a lens to be inserted into the eyeball of the person to be operated on through the lens power determination unit 3300.

The output unit may output a lens power suitable for the eyeball of the person to be operated on according to a learning method of the lens power determination model.

According to an embodiment, when the lens power determination model is implemented in the form of a regression, the output unit may output a lens power suitable for target vision of the eyeball of the person to be operated on. It is possible to output a lens power with the highest probability, which is suitable for the eyeball of the person to be operated on, among a plurality of lens powers. This is merely an example, and not limited thereto. The lens determination model may be implemented using a classifier. In this case, it is possible to output a lens power suitable for the eyeball of the person to be operated on among a plurality of standardized lens powers.

5.2. Lens Power Determination Process

Figure 24:
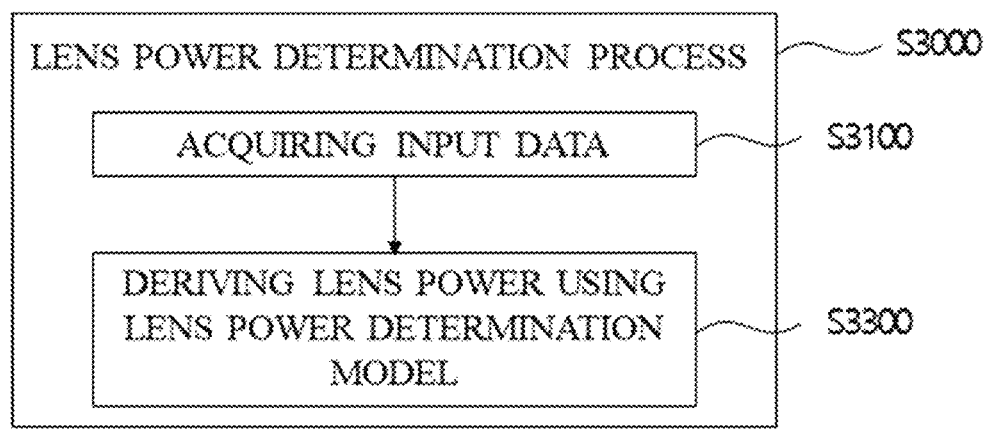
FIG. 24 is a diagram of a lens power determination process according to an embodiment.

FIG. 24 is a flowchart illustrating a lens power determination process S3000. Referring to FIG. 24, the lens power determination process S3000 may include acquiring an input data such as a plurality of examination data of a person to be operated on (S3100) and deriving a lens power using the lens power determination model (S3300). The lens power determination process S3000 may be performed by the lens power determination module 3000 described above with reference to FIG. 2.

Specifically, in operation S3100 of acquiring the input data, the input data may include a plurality of examination data which are acquired from a plurality of examinations related to measurement of an eyeball of the person to be operated on. In an embodiment, the plurality of examinations related to the measurement of the eyeball may include a slit lamp microscopic examination, a fundus examination, an automatic refraction and corneal curvature examination, a corneal topography examination, and the like.

In an embodiment, the plurality of examination data may include uncorrected vision, a location of a coma, conical astigmatism, lenticular astigmatism, a ratio of myopia and astigmatism, and the like.

In an embodiment, the input data may include expected conical incision information of the person to be operated on. For example, the expected corneal incision information may include a conical incision degree, a corneal incision location, a conical incision direction, and the like in a conical incision process of the person to be operated on.

Figure 25:
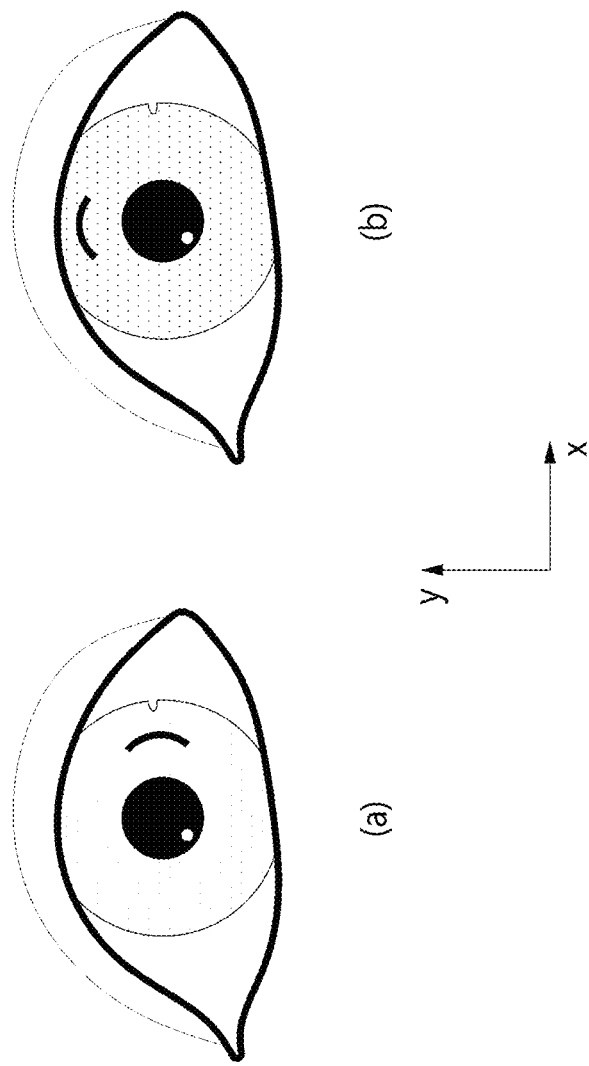

In the determining of the lens power, corneal incision information may be considered. FIG. 25 shows diagrams for describing corneal incision information. Specifically, (a) of FIG. 25 is an exemplary schematic diagram illustrating a corneal incision when astigmatism is not corrected, and (b) of FIG. 25 is an exemplary schematic diagram illustrating a corneal incision when astigmatism is corrected.

Referring to (a) of FIG. 25, in an embodiment, when astigmatism is not corrected during a vision correction of a person to be operated on, a conical incision direction may be an x-axis direction with respect to a pupil. In addition, a corneal incision degree may be a quarter of a length of the pupil.

Referring to (b) of FIG. 25, in an embodiment, when astigmatism is corrected during a vision correction of a person to be operated on, a conical incision direction may be a y-axis direction with respect to a pupil. In addition, a corneal incision degree may be a quarter of a length of the pupil.

FIG. 25 illustrates an example that occurs in a corneal incision process of the person to be operated on, but not limited thereto, and this may vary according to a degree of astigmatism and an astigmatism rate of the person to be operated on.

In an embodiment, in addition to examination data, expected corneal incision information as described with reference to FIG. 25 may be inputted to be used as an input data. When the conical incision information is inputted, the lens power determination unit may determine a lens power in consideration of the corneal incision information.

5.3. Embodiments

Figure 26:
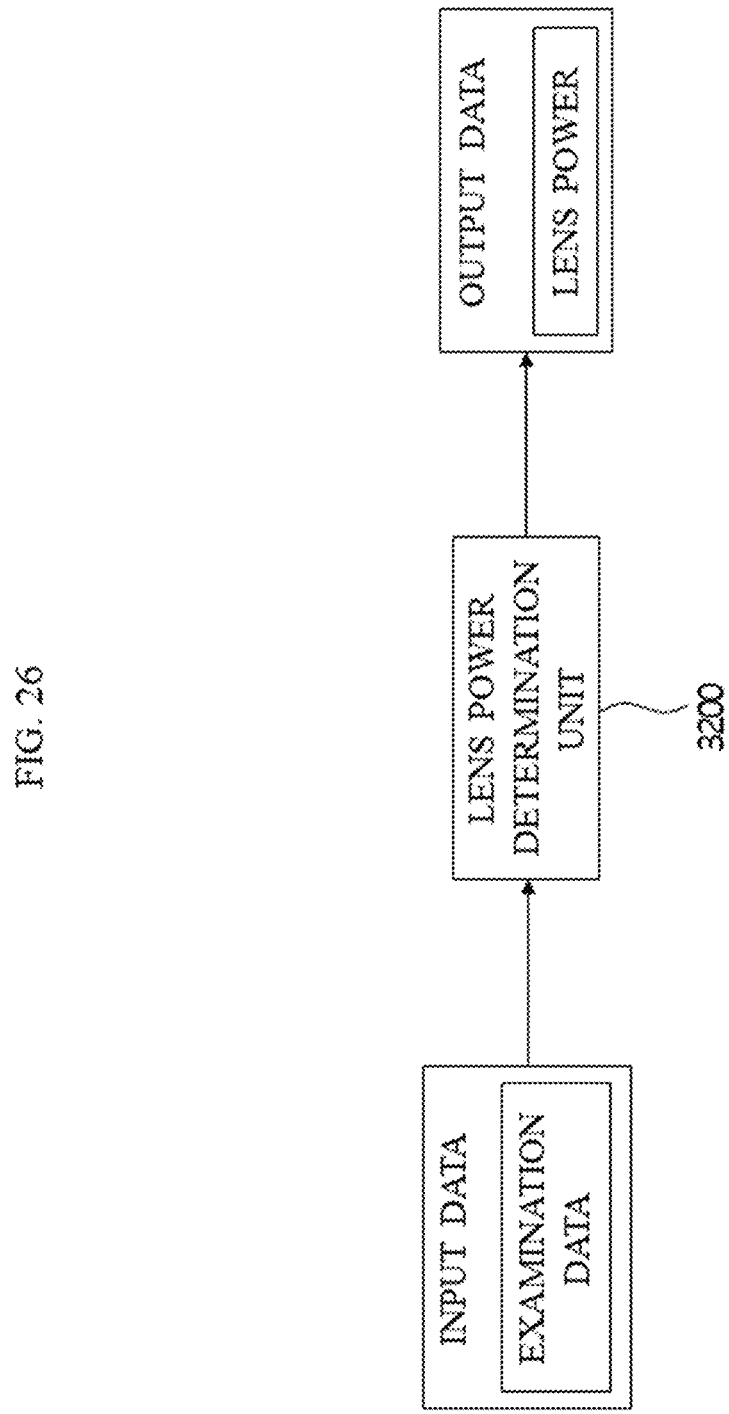
FIG. 26 is a diagram illustrating the determination of a lens power according to an embodiment.

FIG. 26 is a diagram illustrating the determination of a lens power according to an embodiment. Referring to FIG. 26, the lens power determination unit 3300 may output a lens power using a plurality of examination data of a person to be operated on as an input data.

In an embodiment, when the examination data is inputted to the lens power determination model 130, the lens power determination module 3000 may output the lens power.

In an embodiment, the lens power determination model 130 may be trained using leaning data for inputting examination data and outputting a lens power. The training operation S100 described with reference to FIG. 8 may be applied unchanged to a training operation of the lens power determination model.

Although not shown, in an embodiment, the lens power determination unit 3300 may output a lens power and corneal incision information using the examination data of the person to be operated on as an input data. In a corneal incision process, an expected lens power may be outputted concurrently with corneal incision information such as a conical incision degree, a cornea incision location, and a corneal incision degree, thereby outputting a lens power in consideration of factors such as astigmatism corrected according to the corneal incision information.

In an embodiment, the lens power determination model 130 may be trained using learning data for inputting examination data and outputting a lens power and corneal incision information. The training operation S100 described with reference to FIG. 8 may be applied unchanged to a training operation of the lens power determination model.

Although not shown, in an embodiment, the lens power determination unit 3300 may output a lens power, corneal incision information, and astigmatism parameters such as an SIA value caused by surgery using the examination data of the person to be operated on as an input data. In a corneal incision process, an expected lens power may be outputted concurrently with corneal incision information and astigmatism parameters such as an SIA value caused by surgery, thereby outputting a lens power in consideration of factors such as astigmatism corrected according to the corneal incision information and astigmatism caused by surgery.

In an embodiment, the lens power determination model 130 may be trained using learning data for inputting examination data and outputting a lens power, corneal incision information, and astigmatism parameters such as an SIA value caused by surgery. The training operation S100 described with reference to FIG. 8 may be applied unchanged to a training operation of the lens power determination model.

Figure 27:
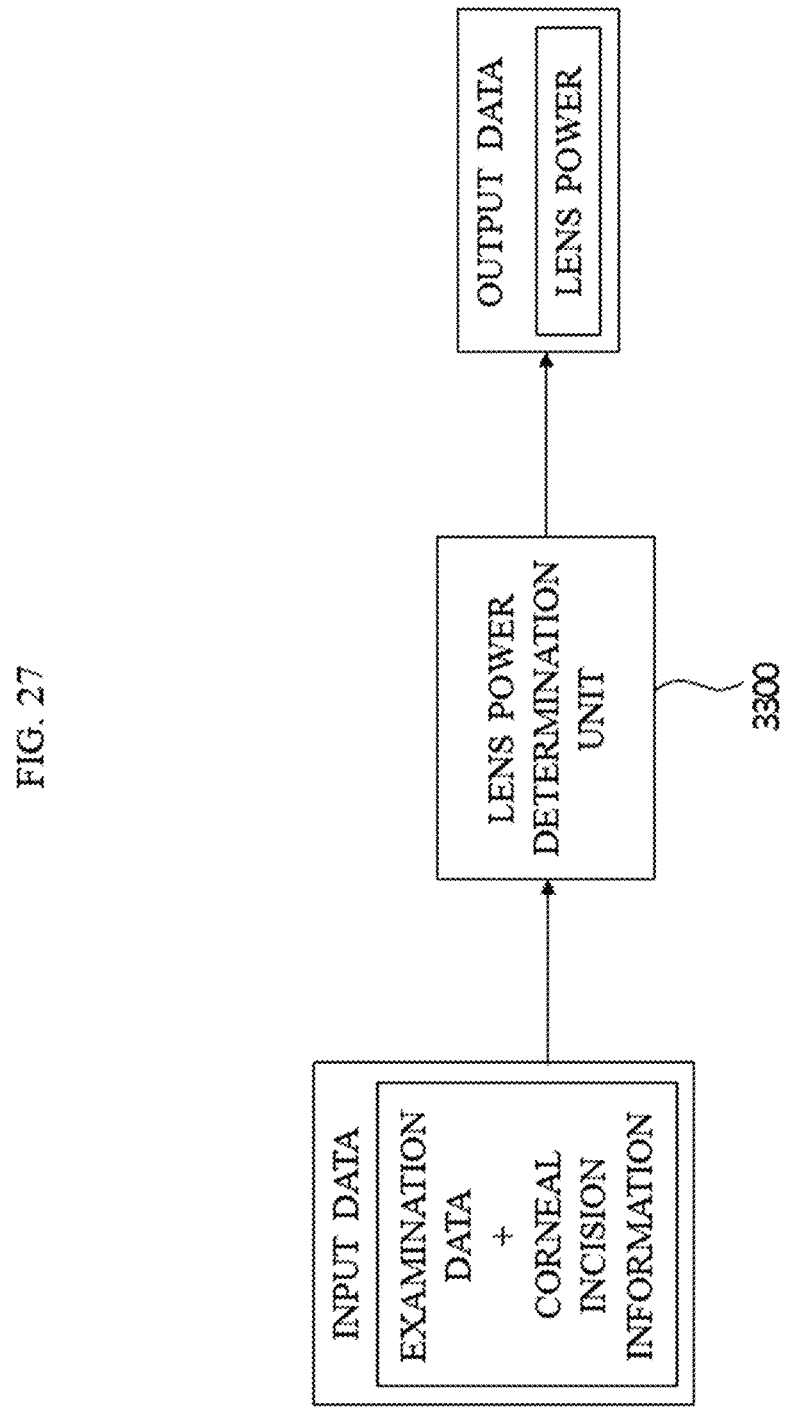
FIG. 27 is a diagram illustrating the determination of a lens power according to another embodiment.

FIG. 27 is a diagram illustrating the determination of a lens power according to another embodiment. Referring to FIG. 27, the lens power determination unit 3300 may output a lens power using a plurality of examination data and corneal incision information of a person to be operated on as an input data.

In an embodiment, the lens power determination model 130 may be trained using learning data for inputting examination data and corneal incision information and outputting a lens power. The training operation S100 described with reference to FIG. 8 may be applied unchanged to a training operation of the lens power determination model.

Although not shown, in an embodiment, the lens power determination unit 3300 may output astigmatism parameters such as an SIA value caused by expected surgery using the plurality of pieces of examination data and the conical incision information of the person to be operated on as an input data.

In an embodiment, the lens power determination model 130 may be trained using learning data for inputting examination data and corneal incision information and outputting astigmatism parameters. The training operation S100 described with reference to FIG. 8 may be applied unchanged to a training operation of the lens power determination model.

Although not shown, in an embodiment, the lens power determination unit 3300 may output astigmatism parameters such as an SIA value caused by expected surgery and corneal incision information using the plurality of examination data and the corneal incision information of the person to be operated on as an input data.

In an embodiment, the lens power determination model 130 may be trained using learning data for inputting examination data and corneal incision information and outputting astigmatism parameters and corneal incision information. The training operation S100 described with reference to FIG. 8 may be applied unchanged to a training operation of the lens power determination model.

Methods according to the embodiments may be implemented in the form of program instructions executable through diverse computing devices and may be recorded in computer-readable media. The computer-readable media may include, independently or in combination, program instructions, data files, data structures, and so on. Program instructions recorded in the media may be specially designed and configured for the embodiments or may be generally known by those skilled in the computer software art. Computer-readable recording media may include magnetic media such as hard disks, floppy disks, and magnetic tapes, optical media such as a CD-ROM and DVD, magneto-optical media such as floptical disks, and hardware units, such as a ROM, a RAM, a flash memory, and so on, which are intentionally formed to store and perform program instructions. Program instructions may include high-class language codes executable by computers using interpreters, as well as machine language codes likely made by compilers. The hardware units may be configured to function as one or more software modules for performing the operations according to the embodiments of the present disclosure, and vice versa.

While features and configurations of the present invention have been described with reference to the embodiments thereof, the present invention is not limited thereto. It is apparent to those skilled in the art that various changes and modifications thereof may be made within the spirit and scope of the present invention, and therefore it is to be understood that such changes and modifications belong to the scope of the appended claims.

The invention claimed is:

1. A method, performed by one or more processors, for determining an implantable collamer lens (ICL) for ICL implant surgery, the method comprising:
    obtaining examination data of a person to be operated on, wherein the obtained examination data of the person includes an ATA (angle-to-angle) distance corresponding to the eye of the person;
    selecting an ICL size of an ICL to be inserted into an eyeball of the person from among a plurality of ICL sizes by inputting the ATA distance to a lens size determination model, wherein the lens size determination model determines the ICL size corresponding to the ATA distance based on probabilities of the plurality of ICL sizes for the ATA distance;
    selecting an ICL power of the ICL from among a plurality of ICL powers by inputting the obtained examination data and corneal incision data of the person to a lens power determination model, wherein the obtained examination data further includes at least one of a refractive error, an astigmatism axis, or an astigmatism direction parameter measured from the eye of the person, wherein the lens power determination model determines the ICL power corresponding to the obtained examination data and the corneal incision data based on probabilities of the plurality of ICL powers for the obtained examination data and the corneal incision data; and
    outputting the selected ICL size and the selected ICL power for performing ICL implant surgery,
    wherein the lens size determination model is trained based on a plurality of ATA distances of first patients who have previously undergone ICL implant surgery and a plurality of size data of ICLs inserted into eyeballs of the first patients such that when an ATA distance is inputted, the lens size determination model outputs an ICL size having the highest probability with respect to the inputted ATA distance, and
    wherein the lens power determination model is trained based on a plurality of examination data of second patients who have previously undergone ICL implant surgery, a plurality of corneal incision data of the second patients, and a plurality of power data of ICLs of the second patients such that when examination data and corneal incision data are inputted, the lens power determination model outputs an ICL power having the highest probability with respect to the inputted examination data and inputted corneal incision data.

2. The method of claim 1,
    wherein the selecting of the ICL size further comprises calculating a reliability of an accuracy of the ICL size derived according to the ATA distance.

3. The method of claim 1,
    wherein the corneal incision data of the person is incision data expected during a corneal incision process of the person's ICL implant surgery.

4. The method of claim 1,
    wherein the plurality of corneal incision data of the second patients includes at least one selected from the group of a corneal incision method, a corneal incision location, a corneal incision direction, a corneal incision degree, a location of coma, a corneal astigmatism, a lenticular astigmatism, a ratio of myopia and astigmatism during a corneal incision process of the ICL implant surgery.

5. A non-transitory computer-readable recording medium in which a program for performing the method of claim 1 is recorded.

6. A device for determining an implantable collamer lens (ICL) for ICL implant surgery, the device comprising:
    a memory for storing examination data of a person to be operated on, wherein the examination data of the person includes an ATA (angle-to-angle) distance corresponding to the eye of the person; and
    a processor configured to:
    obtain the stored examination data of the person from the memory,
    select an ICL size of an ICL to be inserted into an eyeball of the person from among a plurality of ICL sizes by inputting the ATA distance to a lens size determination model, wherein the lens size determination model determines the ICL size corresponding to the ATA distance based on probabilities of the plurality of ICL sizes for the ATA distance,
    select an ICL power of the ICL from among a plurality of ICL powers by inputting the obtained examination data and corneal incision data of the person to a lens power determination model, wherein the obtained examination data further includes at least one of a refractive error, an astigmatism axis, or an astigmatism direction parameter measured from the eye of the person, wherein the lens power determination model determines the ICL power corresponding to the obtained examination data and the corneal incision data based on probabilities of the plurality of ICL powers for the obtained examination data and the corneal incision data, and output the selected ICL size and the selected ICL power for performing ICL implant surgery, wherein the lens size determination model is trained based on a plurality of ATA distances of first patients who have previously undergone ICL implant surgery and a plurality of size data of ICLs inserted into eyeballs of the first patients such that when an ATA distance is inputted, the lens size determination model outputs an ICL size having the highest probability with respect to the inputted ATA distance, and wherein the lens power determination model is trained based on a plurality of examination data of second patients who have previously undergone ICL implant surgery, a plurality of corneal incision data of the second patients, and a plurality of power data of ICLs of the second patients such that when examination data and corneal incision data are inputted, the lens power determination model outputs an ICL power having the highest probability with respect to the inputted examination data and inputted corneal incision data.

* * * * *